(12) United States Patent
Johnson et al.

(10) Patent No.: US 11,421,285 B2
(45) Date of Patent: Aug. 23, 2022

(54) METHOD FOR DIRECT MICROBIAL IDENTIFICATION

(71) Applicant: Quest Diagnostics Investments Incorporated, Wilmington, DE (US)

(72) Inventors: Erik P. Johnson, Oceanside, CA (US); Nik Isely, Moraga, CA (US); Jamie L. Platt, San Juan Capistrano, CA (US); Martin Siaw, Irvine, CA (US); Ron M. Kagen, Rancho Santa Margarita, CA (US); Dale A. Schwab, Carlsbad, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 886 days.

(21) Appl. No.: 15/315,877

(22) PCT Filed: Jun. 4, 2015

(86) PCT No.: PCT/US2015/034202
§ 371 (c)(1),
(2) Date: Dec. 2, 2016

(87) PCT Pub. No.: WO2015/187953
PCT Pub. Date: Dec. 10, 2015

(65) Prior Publication Data
US 2017/0191116 A1    Jul. 6, 2017

Related U.S. Application Data

(60) Provisional application No. 62/007,663, filed on Jun. 4, 2014.

(51) Int. Cl.
*C12Q 1/68* (2018.01)
*C12Q 1/689* (2018.01)
*G16B 30/00* (2019.01)
*C12Q 1/686* (2018.01)
*C12Q 1/6869* (2018.01)
*C12Q 1/6895* (2018.01)

(52) U.S. Cl.
CPC ............ *C12Q 1/689* (2013.01); *C12Q 1/686* (2013.01); *C12Q 1/6869* (2013.01); *C12Q 1/6895* (2013.01); *G16B 30/00* (2019.02); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 6,251,606 B1 | 6/2001 | Hseu et al. |
| 2010/0273219 A1 | 10/2010 | May et al. |
| 2013/0012399 A1 | 1/2013 | Myers et al. |
| 2014/0141993 A1 | 5/2014 | Isshiki et al. |

OTHER PUBLICATIONS

Esfahani et al., "Rapid and accurate identification of *Mycobacterium tuberculosis* complex and common non-tuberculous *Mycobacteria* by multiplex real-time PCR targeting different housekeeping genes," Curr. Microbiol., vol. 65, No. 5, pp. 493-499, Jul. 2014.
Meyer et al., "Parallel tagged sequencing on the 454 platform," Nat. Protoc., vol. 3, No. 2, pp. 267-276, Feb. 2008.
International Search Report dated Nov. 27, 2015 in application No. PCT/US2015/34202.

*Primary Examiner* — Jehanne S Sitton
(74) *Attorney, Agent, or Firm* — Foley & Lardner LLP

(57) ABSTRACT

Described herein are methods for direct detection of microbial agent(s) in a polymicrobial sample, such as a biological sample from a human, without culturing the microbial agent(s). The direct detection can identify mixtures of bacteria and/or fungi in the sample. Also described are primer sequences and amplification techniques for performing the direct detection methods.

13 Claims, 4 Drawing Sheets
Specification includes a Sequence Listing.

Adapters can also be added to opposite ends for bi-directional sequencing

```
                        SEQUENCE LISTING

<160> NUMBER OF SEQ ID NOS: 338

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccatctcatc cctgcgtgtc tccgactcag                                    30

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctctctatg ggcagtcggt gat                                           23

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
                              primer

<400> SEQUENCE: 3
acactgacga catggttcta ca                                            22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tacggtagca gagacttggt ct                                            22

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgagtgcgt                                                          10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgctcgaca                                                          10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agacgcactc                                                          10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcactgtag                                                          10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 9
atcagacacg                                                              10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atatcgcgag                                                              10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtgtctcta                                                              10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcgcgtgtc                                                              10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tagtatcagc                                                              10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tctctatgcg                                                              10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 15
tgatacgtct                                                           10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tactgagcta                                                           10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catagtagtg                                                           10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgagagatac                                                           10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atacgacgta                                                           10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcacgtacta                                                           10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
```
cgtctagtac                                                          10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tctacgtagc                                                          10

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccatctcatc cctgcgtgtc tccgactcag acgagtgcgt                          40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccatctcatc cctgcgtgtc tccgactcag acgctcgaca                          40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccatctcatc cctgcgtgtc tccgactcag agacgcactc                          40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccatctcatc cctgcgtgtc tccgactcag agcactgtag                          40

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccatctcatc cctgcgtgtc tccgactcag atcagacacg        40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccatctcatc cctgcgtgtc tccgactcag atatcgcgag        40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccatctcatc cctgcgtgtc tccgactcag cgtgtctcta        40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccatctcatc cctgcgtgtc tccgactcag ctcgcgtgtc        40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccatctcatc cctgcgtgtc tccgactcag tagtatcagc        40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccatctcatc cctgcgtgtc tccgactcag tctctatgcg        40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccatctcatc cctgcgtgtc tccgactcag tgatacgtct        40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccatctcatc cctgcgtgtc tccgactcag tactgagcta                            40

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccatctcatc cctgcgtgtc tccgactcag catagtagtg                            40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccatctcatc cctgcgtgtc tccgactcag cgagagatac                            40

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccatctcatc cctgcgtgtc tccgactcag atacgacgta                            40

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccatctcatc cctgcgtgtc tccgactcag tcacgtacta                            40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acgcactcgt ctgagtcgga gacacgcagg gatgagatgg                            40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tgtcgagcgt ctgagtcgga gacacgcagg gatgagatgg                                 40

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gagtgcgtct ctgagtcgga gacacgcagg gatgagatgg                                 40

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctacagtgct ctgagtcgga gacacgcagg gatgagatgg                                 40

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgtgtctgat ctgagtcgga gacacgcagg gatgagatgg                                 40

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctcgcgatat ctgagtcgga gacacgcagg gatgagatgg                                 40

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tagagacacg ctgagtcgga gacacgcagg gatgagatgg                                 40

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
gacacgcgag ctgagtcgga gacacgcagg gatgagatgg                    40

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gctgatacta ctgagtcgga gacacgcagg gatgagatgg                    40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
cgcatagaga ctgagtcgga gacacgcagg gatgagatgg                    40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
agacgtatca ctgagtcgga gacacgcagg gatgagatgg                    40

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
tagctcagta ctgagtcgga gacacgcagg gatgagatgg                    40

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
cactactatg ctgagtcgga gacacgcagg gatgagatgg                    40

<210> SEQ ID NO 52

<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
gtatctctcg ctgagtcgga gacacgcagg gatgagatgg    40

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
tacgtcgtat ctgagtcgga gacacgcagg gatgagatgg    40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
tagtacgtga ctgagtcgga gacacgcagg gatgagatgg    40

<210> SEQ ID NO 55
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ccatctcatc cctgcgtgtc tccgactcag acgagtgcgt acactgacga catggttcta      60
ca                                                                    62

<210> SEQ ID NO 56
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ccatctcatc cctgcgtgtc tccgactcag acgctcgaca acactgacga catggttcta      60
ca                                                                    62

<210> SEQ ID NO 57
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ccatctcatc cctgcgtgtc tccgactcag agacgcactc acactgacga catggttcta      60
ca                                                                    62

<210> SEQ ID NO 58
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccatctcatc cctgcgtgtc tccgactcag agcactgtag acactgacga catggttcta      60
ca                                                                    62

<210> SEQ ID NO 59
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccatctcatc cctgcgtgtc tccgactcag atcagacacg acactgacga catggttcta      60
ca                                                                    62

<210> SEQ ID NO 60
<211> LENGTH: 62

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ccatctcatc cctgcgtgtc tccgactcag atatcgcgag acactgacga catggttcta      60
ca                                                                    62

<210> SEQ ID NO 61
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccatctcatc cctgcgtgtc tccgactcag cgtgtctcta acactgacga catggttcta      60
ca                                                                    62

<210> SEQ ID NO 62
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ccatctcatc cctgcgtgtc tccgactcag ctcgcgtgtc acactgacga catggttcta      60
ca                                                                    62

<210> SEQ ID NO 63
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ccatctcatc cctgcgtgtc tccgactcag tagtatcagc acactgacga catggttcta      60
ca                                                                    62

<210> SEQ ID NO 64
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ccatctcatc cctgcgtgtc tccgactcag tctctatgcg acactgacga catggttcta      60
ca                                                                    62

<210> SEQ ID NO 65
<211> LENGTH: 62
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 65
ccatctcatc cctgcgtgtc tccgactcag tgatacgtct acactgacga catggttcta     60
ca                                                                    62

<210> SEQ ID NO 66
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccatctcatc cctgcgtgtc tccgactcag tactgagcta acactgacga catggttcta     60
ca                                                                    62

<210> SEQ ID NO 67
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccatctcatc cctgcgtgtc tccgactcag catagtagtg acactgacga catggttcta     60
ca                                                                    62

<210> SEQ ID NO 68
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ccatctcatc cctgcgtgtc tccgactcag cgagagatac acactgacga catggttcta     60
ca                                                                    62

<210> SEQ ID NO 69
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ccatctcatc cctgcgtgtc tccgactcag atacgacgta acactgacga catggttcta     60
ca                                                                    62

<210> SEQ ID NO 70
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

```
ccatctcatc cctgcgtgtc tccgactcag tcacgtacta acactgacga catggttcta    60
ca                                                                   62
```

<210> SEQ ID NO 71
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

```
cctctctatg ggcagtcggt gattacggta gcagagactt ggtct              45
```

<210> SEQ ID NO 72
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

```
ccatctcatc cctgcgtgtc tccgactcag acgagtgcgt tacggtagca gagacttggt    60
ct                                                                   62
```

<210> SEQ ID NO 73
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73

```
ccatctcatc cctgcgtgtc tccgactcag acgctcgaca tacggtagca gagacttggt    60
ct                                                                   62
```

<210> SEQ ID NO 74
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74

```
ccatctcatc cctgcgtgtc tccgactcag agacgcactc tacggtagca gagacttggt    60
ct                                                                   62
```

<210> SEQ ID NO 75
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75

```
ccatctcatc cctgcgtgtc tccgactcag agcactgtag tacggtagca gagacttggt    60
ct                                                                   62
```

<210> SEQ ID NO 76

```
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccatctcatc cctgcgtgtc tccgactcag atcagacacg tacggtagca gagacttggt    60
ct                                                                   62

<210> SEQ ID NO 77
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ccatctcatc cctgcgtgtc tccgactcag atatcgcgag tacggtagca gagacttggt    60
ct                                                                   62

<210> SEQ ID NO 78
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ccatctcatc cctgcgtgtc tccgactcag cgtgtctcta tacggtagca gagacttggt    60
ct                                                                   62

<210> SEQ ID NO 79
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ccatctcatc cctgcgtgtc tccgactcag ctcgcgtgtc tacggtagca gagacttggt    60
ct                                                                   62

<210> SEQ ID NO 80
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ccatctcatc cctgcgtgtc tccgactcag tagtatcagc tacggtagca gagacttggt    60
ct                                                                   62

<210> SEQ ID NO 81
<211> LENGTH: 62
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 81
ccatctcatc cctgcgtgtc tccgactcag tctctatgcg tacggtagca gagacttggt    60
ct                                                                   62

<210> SEQ ID NO 82
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ccatctcatc cctgcgtgtc tccgactcag tgatacgtct tacggtagca gagacttggt    60
ct                                                                   62

<210> SEQ ID NO 83
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ccatctcatc cctgcgtgtc tccgactcag tactgagcta tacggtagca gagacttggt    60
ct                                                                   62

<210> SEQ ID NO 84
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ccatctcatc cctgcgtgtc tccgactcag catagtagtg tacggtagca gagacttggt    60
ct                                                                   62

<210> SEQ ID NO 85
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ccatctcatc cctgcgtgtc tccgactcag cgagagatac tacggtagca gagacttggt    60
ct                                                                   62

<210> SEQ ID NO 86
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86

```
ccatctcatc cctgcgtgtc tccgactcag atacgacgta tacggtagca gagacttggt    60
ct                                                                   62

<210> SEQ ID NO 87
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ccatctcatc cctgcgtgtc tccgactcag tcacgtacta tacggtagca gagacttggt    60
ct                                                                   62

<210> SEQ ID NO 88
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cctctctatg ggcagtcggt gatacactga cgacatggtt ctaca                    45

<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ggcggacggg tgagtaa                                                   17

<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ggcgaacggg tgagtaa                                                   17

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ggcgcacggg tgagtaa                                                   17

<210> SEQ ID NO 92
<211> LENGTH: 17
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 92
ggcggatggg tgagtaa                                                17

<210> SEQ ID NO 93
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggcaaacggg tgagtaa                                                17

<210> SEQ ID NO 94
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggcgaacggg cgagtaa                                                17

<210> SEQ ID NO 95
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ggcgaacggc tgagtaa                                                17

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
cactgctgcc tcccgtag                                               18

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tactgctgcc tcccgtag                                               18

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gacacggtcc agactcctac                                         20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gacacggccc agactcctac                                         20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gacacggtcc aaactcctac                                         20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gacacggccc aaactcctac                                         20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gatacggccc agactcctac                                         20

<210> SEQ ID NO 103
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
attaccgcgg ctgctg                                             16

<210> SEQ ID NO 104
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
acactgacga catggttcta caggcggacg ggtgagtaa                              39

<210> SEQ ID NO 105
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
acactgacga catggttcta caggcgaacg ggtgagtaa                              39

<210> SEQ ID NO 106
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
acactgacga catggttcta caggcgcacg ggtgagtaa                              39

<210> SEQ ID NO 107
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
acactgacga catggttcta caggcggatg ggtgagtaa                              39

<210> SEQ ID NO 108
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
acactgacga catggttcta caggcaaacg ggtgagtaa                              39

<210> SEQ ID NO 109
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
acactgacga catggttcta caggcgaacg ggcgagtaa                              39

<210> SEQ ID NO 110
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acactgacga catggttcta caggcgaacg gctgagtaa         39

<210> SEQ ID NO 111
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
tacggtagca gagacttggt ctcactgctg cctcccgtag         40

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tacggtagca gagacttggt cttactgctg cctcccgtag         40

<210> SEQ ID NO 113
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acactgacga catggttcta cagacacggt ccagactcct ac         42

<210> SEQ ID NO 114
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
acactgacga catggttcta cagacacggc ccagactcct ac         42

<210> SEQ ID NO 115
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
acactgacga catggttcta cagacacggt ccaaactcct ac         42

<210> SEQ ID NO 116
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
acactgacga catggttcta cagacacggc ccaaactcct ac                          42

<210> SEQ ID NO 117
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
acactgacga catggttcta cagatacggc ccagactcct ac                          42

<210> SEQ ID NO 118
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
tacggtagca gagacttggt ctattaccgc ggctgctg                               38

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aaactcggtc atttagagga agtaa                                             25

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gatgccggaa ccaagagat                                                    19

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aacctcccac ccgtgtttat                                                   20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
atttcgctgc gttcttcatc                                                   20

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
aaactcggtc atttagagga agtaa                                         25

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gctgcgttct tcatcgatg                                                19

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
atcgagtctt tgaacgcaca                                               20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cctacctgat ccgaggtcaa                                               20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tcgagtcttt gaacgcacat                                               20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
cgggtatccc tacctgatcc                                               20

<210> SEQ ID NO 129
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ccatctcatc cctgcgtgtc tccgactcag acgagtgcgt aaactcggtc atttagagga    60
agtaa                                                                65

<210> SEQ ID NO 130
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
cctctctatg ggcagtcggt gatgatgccg gaaccaagag at                       42

<210> SEQ ID NO 131
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ccatctcatc cctgcgtgtc tccgactcag acgagtgcgt aacctcccac ccgtgtttat    60

<210> SEQ ID NO 132
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cctctctatg ggcagtcggt gatatttcgc tgcgttcttc atc                      43

<210> SEQ ID NO 133
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ccatctcatc cctgcgtgtc tccgactcag acgagtgcgt aaactcggtc atttagagga    60
agtaa                                                                65

<210> SEQ ID NO 134
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cctctctatg ggcagtcggt gatgctgcgt tcttcatcga tg                42

<210> SEQ ID NO 135
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ccatctcatc cctgcgtgtc tccgactcag acgagtgcgt atcgagtctt tgaacgcaca    60

<210> SEQ ID NO 136
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
cctctctatg ggcagtcggt gatcctacct gatccgaggt caa                43

<210> SEQ ID NO 137
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ccatctcatc cctgcgtgtc tccgactcag acgagtgcgt tcgagtcttt gaacgcacat    60

<210> SEQ ID NO 138
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
cctctctatg ggcagtcggt gatcgggtat ccctacctga tcc                43

<210> SEQ ID NO 139
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gcaaggtcac cccgaag                17

<210> SEQ ID NO 140
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140

```
cgatgacgcc cttgttg                                          17

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ggcaaggtca ccccgaagg                                        19

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
aggatcttgc cgatgacg                                         18

<210> SEQ ID NO 143
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gacgccacgg caacaag                                          17

<210> SEQ ID NO 144
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
acgccacggc aacaag                                           16

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
caagtggtgc agcttcagga tg                                    22

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cargtggtgc agcttcakga tg                                    22
```

<210> SEQ ID NO 147
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ggcgccgtcg aacac                                                    15

<210> SEQ ID NO 148
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ggcrccgtcg aacac                                                    15

<210> SEQ ID NO 149
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ggcaccgtcg aacac                                                    15

<210> SEQ ID NO 150
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ggcgccgtcg aacac                                                    15

<210> SEQ ID NO 151
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
caccccggtg ttcgac                                                   16

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ctgggtgatc atcgagtacg                                               20

<210> SEQ ID NO 153
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
ccatctcatc cctgcgtgtc tccgactcag gcaaggtcac cccgaag            47

<210> SEQ ID NO 154
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
cctctctatg ggcagtcggt gatcgatgac gcccttgttg                    40

<210> SEQ ID NO 155
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
ccatctcatc cctgcgtgtc tccgactcag ggcaaggtca ccccgaagg          49

<210> SEQ ID NO 156
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
cctctctatg ggcagtcggt gataggatct tgccgatgac g                  41

<210> SEQ ID NO 157
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
ccatctcatc cctgcgtgtc tccgactcag acgagtgcgt gcaaggtcac cccgaag   57

<210> SEQ ID NO 158
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
cctctctatg ggcagtcggt gatgcaaggt caccccgaag                    40

```
<210> SEQ ID NO 159
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
ccatctcatc cctgcgtgtc tccgactcag cgatgacgcc cttgttg          47

<210> SEQ ID NO 160
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
cctctctatg ggcagtcggt gatggcaagg tcaccccgaa gg               42

<210> SEQ ID NO 161
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
ccatctcatc cctgcgtgtc tccgactcag aggatcttgc cgatgacg         48

<210> SEQ ID NO 162
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
ccatctcatc cctgcgtgtc tccgactcag gacgccacgg caacaag          47

<210> SEQ ID NO 163
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ccatctcatc cctgcgtgtc tccgactcag acgccacggc aacaag           46

<210> SEQ ID NO 164
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
cctctctatg ggcagtcggt gatcaagtgg tgcagcttca ggatg            45

<210> SEQ ID NO 165
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
cctctctatg ggcagtcggt gatcargtgg tgcagcttca kgatg              45

<210> SEQ ID NO 166
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
cctctctatg ggcagtcggt gatggcgccg tcgaacac                      38

<210> SEQ ID NO 167
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cctctctatg ggcagtcggt gatggcrccg tcgaacac                      38

<210> SEQ ID NO 168
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
ccatctcatc cctgcgtgtc tccgactcag acgagtgcgt gacgccacgg caacaag  57

<210> SEQ ID NO 169
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
ccatctcatc cctgcgtgtc tccgactcag acgagtgcgt acgccacggc aacaag   56

<210> SEQ ID NO 170
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
cctctctatg ggcagtcggt gatgacgcca cggcaacaag                    40

<210> SEQ ID NO 171
<211> LENGTH: 39
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
cctctctatg ggcagtcggt gatacgccac ggcaacaag                    39

<210> SEQ ID NO 172
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
ccatctcatc cctgcgtgtc tccgactcag caagtggtgc agcttcagga tg      52

<210> SEQ ID NO 173
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccatctcatc cctgcgtgtc tccgactcag cargtggtgc agcttcakga tg      52

<210> SEQ ID NO 174
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ccatctcatc cctgcgtgtc tccgactcag ggcgccgtcg aacac            45

<210> SEQ ID NO 175
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ccatctcatc cctgcgtgtc tccgactcag ggcrccgtcg aacac            45

<210> SEQ ID NO 176
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
ccatctcatc cctgcgtgtc tccgactcag caccccggtg ttcgac           46

<210> SEQ ID NO 177
<211> LENGTH: 43
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 177
cctctctatg ggcagtcggt gatctgggtg atcatcgagt acg                      43

<210> SEQ ID NO 178
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
ccatctcatc cctgcgtgtc tccgactcag acgagtgcgt caccccggtg ttcgac        56

<210> SEQ ID NO 179
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
cctctctatg ggcagtcggt gatcaccccg gtgttcgac                           39

<210> SEQ ID NO 180
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
ccatctcatc cctgcgtgtc tccgactcag ctgggtgatc atcgagtacg               50

<210> SEQ ID NO 181
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ccttgggacc tggtggtt                                                  18

<210> SEQ ID NO 182
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
ccttaggacc tggtggtt                                                  18

<210> SEQ ID NO 183
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 183
gctttaggtc ctggtggtt                                                19

<210> SEQ ID NO 184
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ccttggggcc tggtggtt                                                 18

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
ccttagggcc tggtggtt                                                 18

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
cttcttcgtc ggcagtcaac                                               20

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
cttcttcatc agcagtcaac c                                             21

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
cttcttcatc agcagttagc                                               20

<210> SEQ ID NO 189
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 189
cttcttcatc agcagtaagc                                               20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
cttcttcatc agctgtcaac                                               20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
cttcttcatc ggctgtcaac                                               20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
cttcctcgtc agcggtcaac                                               20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
cttcttcgtc cgctgtcagc                                               20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
cttcttcatc cgctgttagc                                               20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 195
tgcgacagca tgtattcctt                                               20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
cgcaacagca tgtattcctt                                               20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tgcaacggca tgtattcctt                                               20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ggcaacggca tgtattcctt                                               20

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tgagtttgaa cgacggaatt t                                             21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
tgagttggag cgacggaatt t                                             21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 201
agagtttgaa cggcggaatt t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
agagttagaa cgacggaatt t                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
tgagtttgaa cggcggaatt t                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
tgagttagaa cgacggaatt t                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tgagttagaa cggcggaatt t                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
tgaacatcgg tcaggttatg g                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 207
tgaacattgg tcaggttatg g                                              21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tgaatattgg tcaggttatg g                                              21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tgaatatcgg tcaggttatg g                                              21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
tgaacatcgg acaagttatg g                                              21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tgaacattgg acaggttatg g                                              21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tgaacattgg gcaagttatg g                                              21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
```
tgaatatcgg acaagttatg g                          21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
tgaatattgg tcaagttatg g                          21

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
tgaagtttat catcaaccat gtg                        23

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
tgcaatttat catcaaccat gtg                        23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tgcaacttat catcaaccat gtg                        23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
tgaagcttat catctaccat gtg                        23

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tggagtttat catctaccat gtg                                                23

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
tgaagcttat catcaaccat gtg                                                23

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tgcaatttat cgtcaaccat gtg                                                23

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
tggagcttat catcaaccat gtg                                                23

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
cttcaccaca tggttgatga taa                                                23

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
ctccaccaca tggttgatga taa                                                23

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ctccaccaca tggttgacga taa                                                23

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ctccaccaca tggtagatga taa                                            23

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
cttcaccaca tggtagatga taa                                            23

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
ttctggtaca cctggttttg g                                              21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
ttctggcaca cctggttttg g                                              21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
ttctggaaca cctggttttg g                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
ttctgggaca cctggttttg g                                              21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
ttctggtaca ccaggctttg g                                           21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ttctggtacc cctggttttg g                                           21

<210> SEQ ID NO 234
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
ccatctcatc cctgcgtgtc tccgactcag acgagtgcgt                       40

<210> SEQ ID NO 235
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
ccatctcatc cctgcgtgtc tccgactcag acgagtgcgt                       40

<210> SEQ ID NO 236
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
ccatctcatc cctgcgtgtc tccgactcag acgagtgcgt                       40

<210> SEQ ID NO 237
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
ccatctcatc cctgcgtgtc tccgactcag acgagtgcgt                       40

```
<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
cctctctatg ggcagtcggt gat                                            23

<210> SEQ ID NO 239
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
cctctctatg ggcagtcggt gat                                            23

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
cctctctatg ggcagtcggt gat                                            23

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
cctctctatg ggcagtcggt gat                                            23

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
cctctctatg ggcagtcggt gat                                            23

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
cctctctatg ggcagtcggt gat                                            23

<210> SEQ ID NO 244
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
cctctctatg ggcagtcggt gat                                              23

<210> SEQ ID NO 245
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
ccatctcatc cctgcgtgtc tccgactcag acgagtgcgt                            40

<210> SEQ ID NO 246
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
ccatctcatc cctgcgtgtc tccgactcag acgagtgcgt                            40

<210> SEQ ID NO 247
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
ccatctcatc cctgcgtgtc tccgactcag acgagtgcgt                            40

<210> SEQ ID NO 248
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
ccatctcatc cctgcgtgtc tccgactcag acgagtgcgt                            40

<210> SEQ ID NO 249
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
ccatctcatc cctgcgtgtc tccgactcag acgagtgcgt                            40

<210> SEQ ID NO 250
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
ccatctcatc cctgcgtgtc tccgactcag acgagtgcgt                          40

<210> SEQ ID NO 251
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
ccatctcatc cctgcgtgtc tccgactcag acgagtgcgt                          40

<210> SEQ ID NO 252
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
ccatctcatc cctgcgtgtc tccgactcag acgagtgcgt                          40

<210> SEQ ID NO 253
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ccatctcatc cctgcgtgtc tccgactcag acgagtgcgt                          40

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
cctctctatg ggcagtcggt gat                                            23

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
cctctctatg ggcagtcggt gat                                            23

<210> SEQ ID NO 256
<211> LENGTH: 23
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 256
cctctctatg ggcagtcggt gat                                          23

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
cctctctatg ggcagtcggt gat                                          23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
cctctctatg ggcagtcggt gat                                          23

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
cctctctatg ggcagtcggt gat                                          23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
cctctctatg ggcagtcggt gat                                          23

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
cctctctatg ggcagtcggt gat                                          23

<210> SEQ ID NO 262
<211> LENGTH: 40
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 262
ccatctcatc cctgcgtgtc tccgactcag acgagtgcgt                              40

<210> SEQ ID NO 263
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
ccatctcatc cctgcgtgtc tccgactcag acgagtgcgt                              40

<210> SEQ ID NO 264
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
ccatctcatc cctgcgtgtc tccgactcag acgagtgcgt                              40

<210> SEQ ID NO 265
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
ccatctcatc cctgcgtgtc tccgactcag acgagtgcgt                              40

<210> SEQ ID NO 266
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
ccatctcatc cctgcgtgtc tccgactcag acgagtgcgt                              40

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
cctctctatg ggcagtcggt gat                                                23

<210> SEQ ID NO 268
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 268
cctctctatg ggcagtcggt gat                                             23

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
cctctctatg ggcagtcggt gat                                             23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
cctctctatg ggcagtcggt gat                                             23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
cctctctatg ggcagtcggt gat                                             23

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
cctctctatg ggcagtcggt gat                                             23

<210> SEQ ID NO 273
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
gaaactacgc gagaatttca gaag                                            24

<210> SEQ ID NO 274
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 274
gaaattacgc gagaatttca gaag                                              24

<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
gaaattatgc gagaatttca gaag                                              24

<210> SEQ ID NO 276
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
gaaactatgc gagaatttca gagg                                              24

<210> SEQ ID NO 277
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
cgaagaggtg cagcataagt ag                                                22

<210> SEQ ID NO 278
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
cgtaatggtg ccgcgtatgt tg                                                22

<210> SEQ ID NO 279
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
cgtagaggtg cagaatacgt tg                                                22

<210> SEQ ID NO 280
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ccaatatgga agacatcgta aacg                                              24

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
ccaattccgt atcggtttat c                                                 21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
ccaattccgt attggtttat c                                                 21

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
acttccattt gagcacgttc                                                   20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
acttccattt gggcacgttc                                                   20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
acttccattt gtgcacgttc                                                   20

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 286
gtgaacgtgc tcaaatggaa g                                              21

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
gtgaacgtgc ccaaatggaa g                                              21

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
gtgaacgtgc acaaatggaa g                                              21

<210> SEQ ID NO 289
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
acatagctat cttcttcatc agc                                            23

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
acgtaactat cctcttcatc agc                                            23

<210> SEQ ID NO 291
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
acatagctat cctcttcatc agc                                            23

<210> SEQ ID NO 292
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
```
acatagctat cttcttcgtc agc							23

<210> SEQ ID NO 293
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
acataactgt cttcttcatc agc							23

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
tcggtgagat ggaggtatgg							20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
tcggtgagat ggaagtatgg							20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
tcggtgaaat ggaagtatgg							20

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
ctcggaatga ttctggaaca c							21

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
ctcggaatga ttcaggaaca c                                              21

<210> SEQ ID NO 299
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
gaagaagcag ttcggcaa                                                  18

<210> SEQ ID NO 300
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
gagtcgatga cgatcat                                                   17

<210> SEQ ID NO 301
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
ccacgctcac gctgcagg                                                  18

<210> SEQ ID NO 302
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
cgagcccgag cgcaccag                                                  18

<210> SEQ ID NO 303
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
cgaaggcgag atgggcg                                                   17

<210> SEQ ID NO 304
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
tcgagacgca ccgacg                                                    16

<210> SEQ ID NO 305
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
gtgcaggcga agatcgtcg                                                19

<210> SEQ ID NO 306
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
ccatcgcctc ggcttcg                                                  17

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
ggcggacgtc acactccatt c                                             21

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
ccgtcttcga tagcgattgg gtgg                                          24

<210> SEQ ID NO 309
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
ggttgctcgt gaagacatcc aac                                           23

<210> SEQ ID NO 310
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
caccagtaac gtctgttgta cgg                                           23

<210> SEQ ID NO 311
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
caggcgatga tgttccagtt atcgc                                           25

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
gtagcaacag taccacgtcc agtg                                            24

<210> SEQ ID NO 313
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: a, c, t, g, unknown or other

<400> SEQUENCE: 313
tgtaaaacga cggccagtgc nggrtcytty tcytgrca                             38

<210> SEQ ID NO 314
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
tgtaaaacga cggccagt                                                   18

<210> SEQ ID NO 315
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (29)..(29)
<223> OTHER INFORMATION: a, c, t, g, unknown or other

<400> SEQUENCE: 315
caggaaacag ctatgaccay gsnggnggna arttyra                         37

<210> SEQ ID NO 316
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
caggaaacag ctatgacc                                              18

<210> SEQ ID NO 317
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
cagctgggac atcctggcc                                             19

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
tgagggatgt tgttggtaaa gcac                                       24

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
gtgctttacc aacaacatcc ctca                                       24

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
tgtctttggt ctgggagctg aac                                        23

<210> SEQ ID NO 321
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (48)..(48)
<223> OTHER INFORMATION: Inosine

<400> SEQUENCE: 321
ccatctcatc cctgcgtgtc tccgactcag acgctcgaca agyggcgnac gggtgagtaa        60

<210> SEQ ID NO 322
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (48)..(48)
<223> OTHER INFORMATION: Inosine

<400> SEQUENCE: 322
ccatctcatc cctgcgtgtc tccgactcag agacgcactc agyggcgnac gggtgagtaa        60

<210> SEQ ID NO 323
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (48)..(48)
<223> OTHER INFORMATION: Inosine

<400> SEQUENCE: 323
ccatctcatc cctgcgtgtc tccgactcag agcactgtag agyggcgnac gggtgagtaa        60

<210> SEQ ID NO 324
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (48)..(48)
<223> OTHER INFORMATION: Inosine

<400> SEQUENCE: 324
ccatctcatc cctgcgtgtc tccgactcag atcagacacg agyggcgnac gggtgagtaa        60

<210> SEQ ID NO 325
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (48)..(48)
<223> OTHER INFORMATION: Inosine

<400> SEQUENCE: 325
ccatctcatc cctgcgtgtc tccgactcag atatcgcgag agyggcgnac gggtgagtaa        60

<210> SEQ ID NO 326
<211> LENGTH: 60
<212> TYPE: DNA
<213> ORGANISM: Artificial Sequence
<220> FEATURE:

<223> OTHER INFORMATION: Description of Artificial Sequence: Synthetic
    primer
<220> FEATURE:
<221> NAME/KEY: modified_base
<222> LOCATION: (48)..(48)
<223> OTHER INFORMATION: Inosine

<400> SEQUENCE: 326
ccatctcatc cctgcgtgtc tccgactcag cgtgtctcta agyggcgnac gggtgagtaa    60

<210> SEQ ID NO 327
<211> LENGTH: 60
<212> TYPE: DNA
<213> ORGANISM: Artificial Sequence
<220> FEATURE:
<223> OTHER INFORMATION: Description of Artificial Sequence: Synthetic
    primer
<220> FEATURE:
<221> NAME/KEY: modified_base
<222> LOCATION: (48)..(48)
<223> OTHER INFORMATION: Inosine

<400> SEQUENCE: 327
ccatctcatc cctgcgtgtc tccgactcag ctcgcgtgtc agyggcgnac gggtgagtaa    60

<210> SEQ ID NO 328
<211> LENGTH: 60
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 328
ccatctcatc cctgcgtgtc tccgactcag acgctcgaca actcctacgg gaggcagcag    60

<210> SEQ ID NO 329
<211> LENGTH: 60
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 329
ccatctcatc cctgcgtgtc tccgactcag agacgcactc actcctacgg gaggcagcag    60

<210> SEQ ID NO 330
<211> LENGTH: 60
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 330
ccatctcatc cctgcgtgtc tccgactcag agcactgtag actcctacgg gaggcagcag    60

<210> SEQ ID NO 331
<211> LENGTH: 60
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 331
ccatctcatc cctgcgtgtc tccgactcag atcagacacg actcctacgg gaggcagcag    60

```
<210> SEQ ID NO 332
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
ccatctcatc cctgcgtgtc tccgactcag atatcgcgag actcctacgg gaggcagcag    60

<210> SEQ ID NO 333
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
ccatctcatc cctgcgtgtc tccgactcag cgtgtctcta actcctacgg gaggcagcag    60

<210> SEQ ID NO 334
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
ccatctcatc cctgcgtgtc tccgactcag acgagtgcgt actcctacgg gaggcagcag    60

<210> SEQ ID NO 335
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
acactgacga catggttcta caaaactcgg tcatttagag gaagtaa                  47

<210> SEQ ID NO 336
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
tacggtagca gagacttggt ctgctgcgtt cttcatcgat g                        41

<210> SEQ ID NO 337
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
acactgacga catggttcta caatcgagtc tttgaacgca ca                       42
```

```
<210> SEQ ID NO 338
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
tacggtagca gagacttggt ctcctacctg atccgaggtc aa                            42
```

METHOD FOR DIRECT MICROBIAL IDENTIFICATION

CROSS-REFERENCE TO RELATED APPLICATIONS

This application claims the benefit of U.S. provisional application No. 62/007,663, filed Jun. 4, 2014, the contents of which are incorporated herein by reference in their entirety.

FIELD OF THE INVENTION

Methods for direct detection of microbial agent(s) in a sample, including a mixture of bacterial and fungal microbial agents, are disclosed. Nucleotide sequences and amplification techniques to identify microbial agent(s) in a sample also are described.

BACKGROUND OF THE INVENTION

The following description of the background of the invention is provided simply as an aid in understanding the invention and is not admitted to describe or constitute prior art to the invention.

Microbial agents are currently identified by first culturing the agents using media and growth conditions, and then analyzing morphological/biochemical characteristics or DNA sequencing to determine their identity. Culturing isolates the microbial agents so they can be characterized by phenotypic or genotypic methods, and also provides conditions favorable to grow the microbial agents to produce enough material for analysis.

However, culturing has drawbacks. For example, culturing microbial agents is time consuming and not practical in situations where many different agents are presented in a sample. Moreover, recovering microbial agents from culture can be difficult if the culture conditions are not optimized, proper growth conditions are unknown, or certain agents are overgrown and mask the presence of slow-growing agents. The masking of some microbial agents can prevent correctly identifying all microbial agents in a sample.

The masking of some microbial agents is especially problematic with a biofilm sample (e.g., from a chronic wound, a catheter site infection, or due to periodontal disease) because multiple microbial agents can comprise the biofilm, but the most pathogenic specie(s) may be present in the lowest abundance. As a result, a patient's microbial infections are often treated with antibiotics that are not effective in treating their particular infection because the particular pathogenic species is unknown.

A technique to quickly identify all microbial agents in a sample would allow for quicker and more accurate identification of the source(s) of a microbial infection.

SUMMARY OF THE INVENTION

Provided herein are methods for determining the presence or absence of a microbial agent in a sample, comprising (a) contacting a sample containing sample nucleic acids with an amplification reaction mixture, wherein the amplification reaction mixture primers that specifically amplify at least one target sequence of bacterial 16S rDNA, at least one target sequence of fungal ITS rDNA, and at least one target sequence selected each of *Mycobacterium* rpoB, *Staphylococcus* rpoB, *Streptococcus* rpoB, *Burkholderia* recA, *Enterococcus* tuf, and *Pseudomonas* gvrB, the generate amplification reaction mixture containing the sample nucleic acids; (b) subjecting the amplification reaction mixture containing the sample nucleic acids to polymerase chain reaction (PCR) conditions to generate microbial amplicons; (c) producing adapter-tagged amplicons by attaching the microbial amplicons of step (b), if present, to nucleic acid adapters; (d) amplifying the adapter-tagged amplicons, if present, from step (c) to generate adapter-tagged amplicons; and (e) sequencing the adapter-tagged amplicons, if present, from step (c), wherein a microbial agent is determined to be present in the sample if a microbial amplicon is present and the sequence of the non-adapter portion of an adapter tagged microbial amplicon is at least 90% identical to a nucleotide fragment of bacterial 16S rDNA or fungal ITS rDNA. In some embodiments, the method further comprises identifying the species of bacteria and/or fungus in the sample as *Mycobacterium, Staphylococcus, Streptococcus, Burkholderia, Enterococcus* and/or *Pseudomonas* gvrB. In some embodiments, the reagent mixture further comprises a DNA polymerase and a plurality of free nucleotides comprising adenine, thymine, cytosine and guanine. In some embodiments, the PCR involves (i) heating the reaction mixture to a first predetermined temperature for a first predetermined time to separate the strands of the double stranded DNA from each other, (ii) cooling the reaction mixture to a second predetermined temperature for a second predetermined time under conditions to allow the first and second primers to hybridize with their complementary sequences on the first and second strands of the target DNA, and to allow Taq polymerase to extend the primers, and (iii) repeating steps (i) and (ii) at least 12 times to amplify microbial nucleic acids, if present, in the sample to produce microbial amplicons.

In some embodiments, BLAST (Basic Local Alignment Search Tool) is performed to make a broad identification based on the universal rDNA sequence followed by a BLAST of the taxon specific genes to provide resolution to species level.

In some embodiments, a post-extraction step is performed on the sample nucleic acids to remove human DNA prior to combining with the amplification reaction mixture.

In some embodiments, the amplification reaction mixture comprises primers comprising any of SEQ ID NOs 1-335. In some embodiments, multiple different target regions are amplified in a multiplexed reaction. In some embodiments, each target sequence amplification is performed in a separate, individual PCR reaction.

In some embodiments, primers that specifically amplify at least one target sequence of bacterial 16S rDNA comprise a sequence selected from among SEQ ID NOs 89-103.

In some embodiments, primers that specifically amplify at least one target sequence of fungal ITS rDNA comprise a sequence selected from among SEQ ID NOs 119-128.

In some embodiments, primers that specifically amplify at least one target sequence of *Mycobacterium* rpoB comprise a sequence selected from among SEQ ID NOs 139-152.

In some embodiments, primers that specifically amplify at least one target sequence of *Streptococcus* rpoB comprise a sequence selected from among SEQ ID NOs 181-233.

In some embodiments, primers that specifically amplify at least one target sequence of *Staphylococcus* rpoB comprise a sequence selected from among SEQ ID NOs 273-298.

In some embodiments, primers that specifically amplify at least one target sequence of *Burkholderia* recA comprise a sequence selected from among SEQ ID NOs 299-306.

In some embodiments, primers that specifically amplify at least one target sequence of *Enterococcus* tuf comprise a sequence selected from among SEQ ID NOs 307-312.

In some embodiments, primers that specifically amplify at least one target sequence of *Pseudomonas* gvrB comprise a sequence selected from among SEQ ID NOs 313-320.

In some embodiments, the primers further comprise a tag sequence selected from the group consisting of SEQ ID NO:3 and SEQ ID NO:4.

In some embodiments, the adapter sequence is selected from the group consisting of SEQ ID NO:1 and SEQ ID NO:2.

In some embodiments, the adapters are attached via a primer comprising the adaptor sequence. In some embodiments, the primer comprising the adaptor sequence further comprises a multiplex identifier sequence. In some embodiments, the primer comprising the adaptor sequence further comprises a tag sequence specific for the microbial amplicon. In some embodiments, the tag sequence is selected from the group consisting of SEQ ID NO:3 and SEQ ID NO:4.

In some embodiments, the adapters are attached via enzyme ligation.

In some embodiments, the sample nucleic acids are nucleic acids from a human biological sample. In some embodiments, the biological sample is a urine, sputum, vaginal fluid, sperm, blood or synovial fluid sample Kits are also provided that comprise at least one of the oligonucleotide primers selected from the group consisting of SEQ ID NOs 1-335.

In some embodiments, the primers in a kit as disclosed herein further comprise a multiplex identifier sequence, a tag sequence and/or an adapter sequence. In some embodiments, one primer of a primer pair comprises an MID and both primers in a primer pair comprise adapter sequences. A forward primer and a reverse primer may comprise different adapter sequences. In some embodiments, the adapter sequence is selected from the group consisting of SEQ ID NO: 1 and SEQ ID NO:2. In some embodiments, the primers further comprise a multiplex identifier sequence. In some embodiments, the primers comprises a tag sequence specific for the microbial amplicon. In some embodiments, the tag sequence is selected from the group consisting of SEQ ID NO:3 and SEQ ID NO:4.

BRIEF DESCRIPTION OF THE FIGURES

FIG. 3 differs from FIG. 2 in that the adapters are attached in the opposite orientation.

DETAILED DESCRIPTION OF THE INVENTION

Definitions

Figure 1:
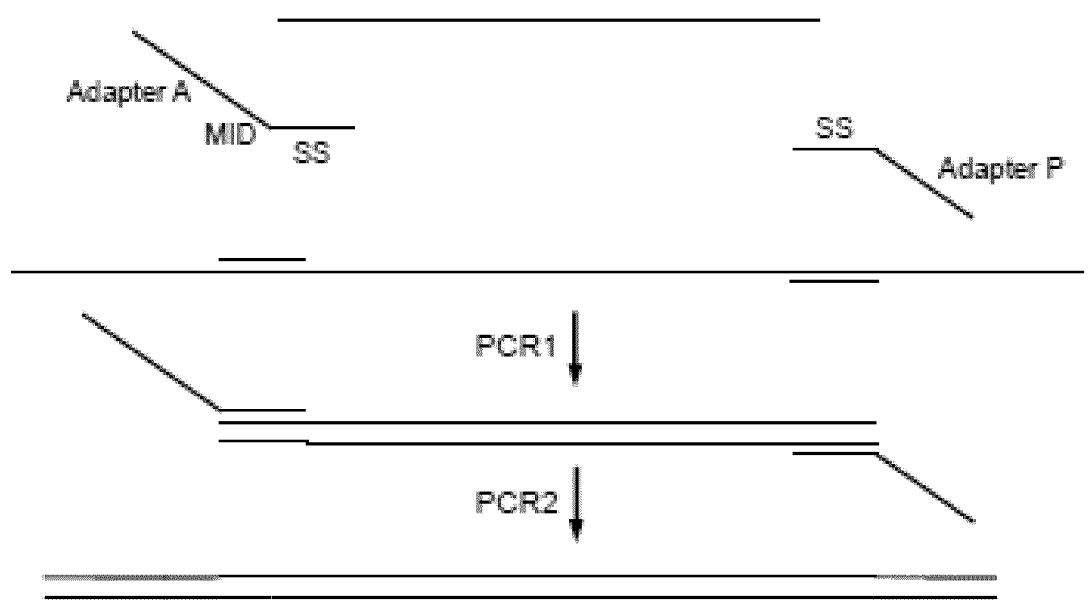
FIG. 1 depicts direct detection of a microbial agent using primers comprising an adapter sequence (Adapter A or Adapter P) and a target specific sequence (SS), with or without a multiplex identifier (MID). Microbial amplicons are generated in a first amplification reaction (PCR1) using primers comprising a target specific sequence (SS). Adapters are attached in a second amplification reaction (PCR2) using the primers comprising an adapter sequence (Adapter A or Adapter P) and a target specific sequence (SS), with or without a multiplex identifier (MID).
Figure 2:
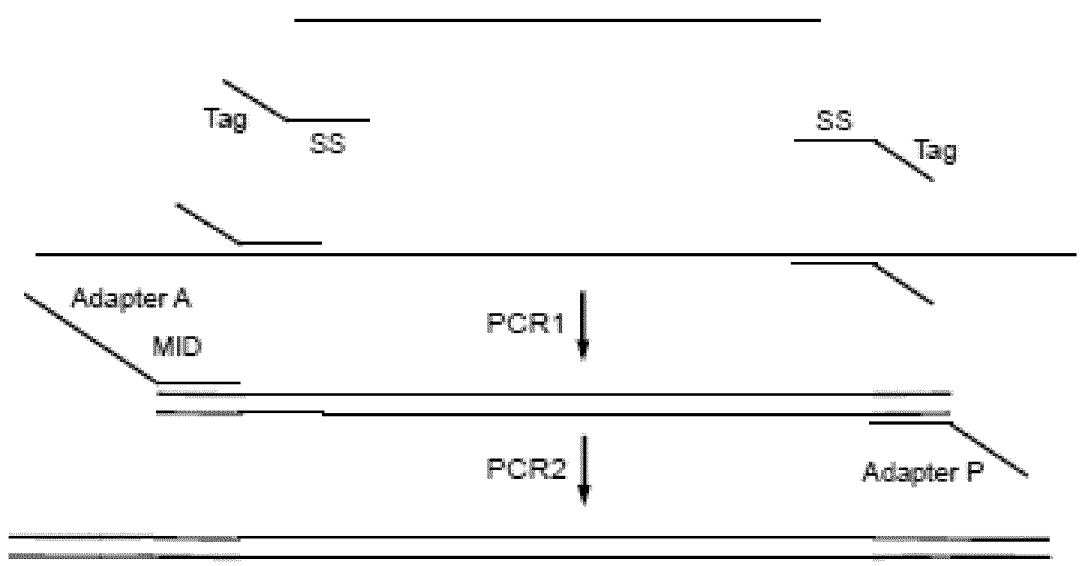
FIG. 2 depicts direct detection of a microbial agent using (i) primers comprising a target specific sequence (SS) and a tag (Tag) and (ii) primers comprising an adapter sequence (Adapter A or Adapter P) and the Tag sequence, with or without a multiplex identifier (MID). Microbial amplicons are generated in a first amplification reaction (PCR1) using primers comprising a target specific sequence (SS) and a tag (Tag). Adapters are attached in a second amplification reaction (PCR2) using the primers comprising an adapter sequence (Adapter A or Adapter P) and the Tag sequence, with or without a multiplex identifier (MID).
Figure 3:
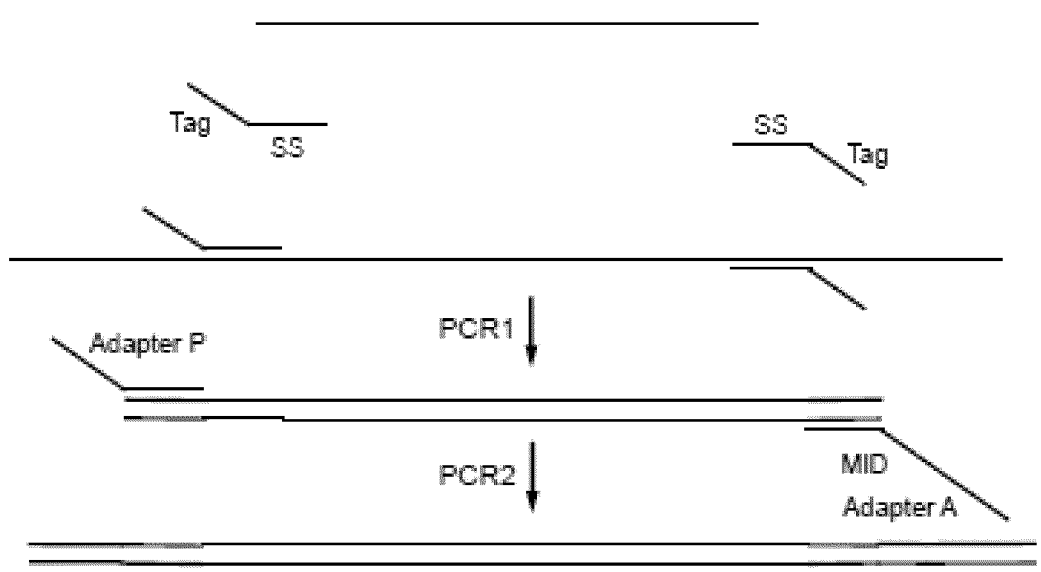
FIG. 3 depicts direct detection of a microbial agent with bi-directional sequencing using (i) primers comprising a target specific sequence (SS) and a tag (Tag) and (ii) primers comprising an adapter sequence (Adapter A or Adapter P) and the Tag sequence, with or without a multiplex identifier (MID).
Figure 4:
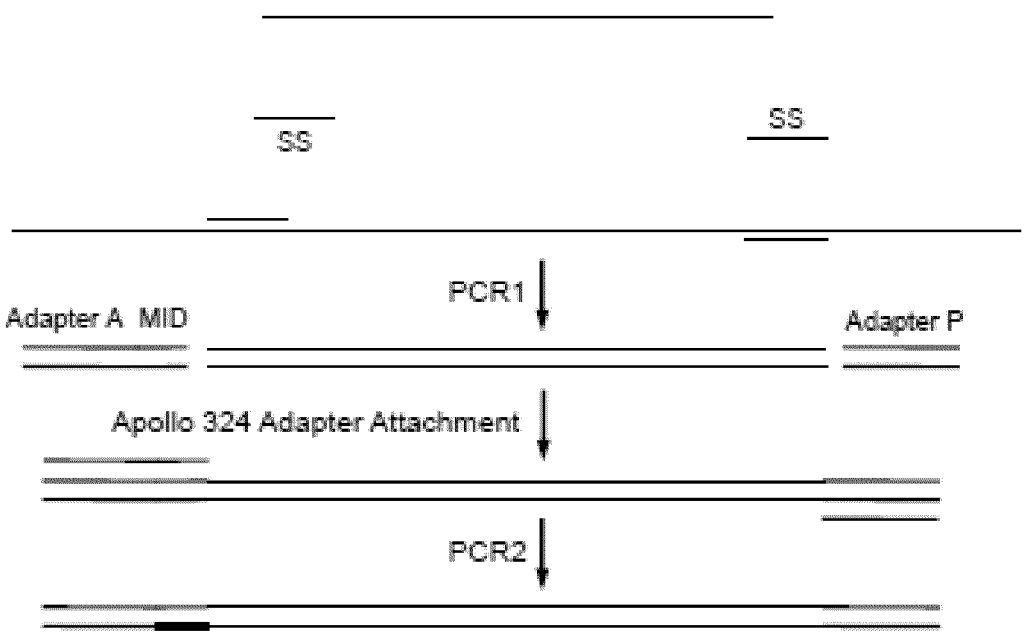
FIG. 4 depicts direct detection of a microbial agent using primers comprising a target specific sequence (SS) in a first amplification reaction (PCR1) and attaching a double stranded adapter sequence (Adapter A or Adapter P), with or without a multiplex identifier (MID), to the microbial amplicon using enzyme ligation (Apollo 324 Adapter Attachment). A second amplification reaction can be performed (PCR1) to further amplify the adapter-tagged amplicon.

The term "amplify" as used herein with respect to nucleic acid sequences, refers to methods that increase the representation of a population of nucleic acid sequences in a sample. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(1 1):E54-E54; Hafner et al., Biotechniques 2001 April; 30(4):852-6, 858, 860 passim; Zhong et al., Biotechniques 2001 April; 30(4): 852-6, 858, 860.

A "nucleic acid" as used herein refers to a nucleic acid that contains a sequence of a microbial gene, mRNA, cDNA or a portion of such a sequence. A nucleic acid may contain the coding region. A nucleic acid may be genomic DNA, cDNA, single stranded DNA or mRNA. In some embodiments, only a single strand of a sample nucleic acid is amplified and/or sequenced. In some embodiments both strands of double stranded DNA are amplified and sequenced. A nucleic acid may be present in a sample, such as a biological sample, or it may be isolated from the sample.

The term "sense strand" as used herein means the strand of double-stranded DNA (dsDNA) that includes at least a portion of a coding sequence of a functional protein. "Antisense strand" means the strand of dsDNA that is the reverse complement of the sense strand.

The terms "complementary" or "complementarity" as used herein with reference to polynucleotides (i.e., a sequence of nucleotides such as an oligonucleotide or a target nucleic acid) refers to the base-pairing rules. The complement of a nucleic acid sequence as used herein refers to nucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-S." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA.

The term "substantially complementary" as used herein means that two sequences hybridize under stringent hybridization conditions. The skilled artisan will understand that substantially complementary sequences need not hybridize along their entire length. In particular, substantially complementary sequences may comprise a contiguous sequence of bases that do not hybridize to a target sequence, positioned 3' or 5' to a contiguous sequence of bases that hybridize under stringent hybridization conditions to a target sequence.

The term "hybridize" as used herein refers to a process where two complementary nucleic acid strands anneal to each other under appropriately stringent conditions. Hybridizations are typically and preferably conducted with probe-length nucleic acid molecules, preferably 20-100 nucleotides in length, more preferably 18-50 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J. In some embodiments, specific hybridization occurs under stringent hybridization conditions.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The term "dosage" or "gene dosage" refers to the number of copies of a gene, or portions of a gene, present in a sample.

The term "primer" as used herein means a sequence of nucleic acid, including DNA, which hybridizes to a substantially complementary target sequence and is recognized by DNA polymerase to begin DNA replication. The term primer as used herein includes all forms of primers that may be synthesized, including peptide nucleic acid primers, locked nucleic acid primers, phosphorothioate modified primers, labeled primers, and the like.

The term "forward primer" as used herein means a primer that anneals to the anti-sense strand of dsDNA. A "reverse primer" anneals to the sense-strand of dsDNA.

The term "specific" as used herein in reference to an oligonucleotide primer means that the primer hybridization sequence of the primer has at least 12 bases of sequence identity with a portion of the nucleic acid to be amplified when the oligonucleotide and the nucleic acid are aligned. A primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

The term "flanking" as used herein with regard to primers means that a primer hybridizes to a target nucleic acid adjoining a region of interest sought to be amplified on the target. The skilled artisan will understand that preferred primers are pairs of primers that hybridize 5' from a region of interest, one on each strand of a target double stranded DNA molecule, such that nucleotides may be added to the 3' end of the primer by a suitable DNA polymerase. Primers that flank an exon are generally designed not to anneal to the exon sequence but rather to anneal to sequence that adjoins the exon (e.g., intron sequence). However, in some cases, an amplification primer may be designed to anneal to the exon sequence.

"Sequencing depth" or "read depth" as used herein refers to the number of times a sequence has been sequenced (i.e., the depth of sequencing). As an example, read depth can be determined by aligning multiple sequencing run results and counting the start position of reads in nonoverlapping windows of a certain size (e.g., 100 bp). Copy number variation can be determined based on read depth using methods known in the art. For example, using a method described in Yoon et al., Genome Research 2009 September; 19(9): 1586-1592; Xie et al., BMC Bioinformatics 2009 Mar. 6; 10:80; or Medvedev et al., Nature Methods 2009 November; 6(11 Suppl):S13-20. Use of this type of method and analysis is referred to as a "read depth approach."

"Coverage depth" refers to the number of nucleotides from sequencing reads that are mapped to a given position.

The term "isolated" as used herein with respect to a nucleic acid (e.g., RNA, DNA or a mixed polymer) is one which is substantially separated from other cellular components which naturally accompany such nucleic acid. The term embraces a nucleic acid sequence which has been removed from its naturally occurring environment, and includes recombinant or cloned DNA isolates, oligonucleotides, and chemically synthesized analogs or analogs biologically synthesized by heterologous systems.

The term "substantially pure" as used herein means a nucleic acid, represents more than 50% of the nucleic acid in a sample. The nucleic acid sample may exist in solution or as a dry preparation.

The term "coding sequence" as used herein means a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced there from.

The term "non-coding sequence" as used herein means a sequence of a nucleic acid or its complement, or a part thereof, which is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

The term "about" as used herein means in quantitative terms plus or minus 10%.

Methods

Described herein are methods for direct detection of one or more microbial agents (i.e., microbial agent(s)) in a sample. Direct detection refers to identifying microbial agent(s) in a sample without culturing the sample. Culturing as used herein refers to any technique in which microbial agents in a sample are sustained and/or expanded in vitro, for example, using media and/or growth conditions. In some embodiments, direct detection refers to identifying a mixture of different microbial agents in a sample, such as a mixture of different bacteria, a mixture of different fungi, and a mixture of bacterium/bacteria and fungus/fungi.

In some embodiments, methods for direct detection include extracting nucleic acid from a sample without separating different types of nucleic acid, such as nucleic acid from different types of microbial agents. In some embodiments, methods for direct detection include identifying microbial agent(s) in a sample after extracting nucleic acid from the sample. In specific embodiments, direct detection includes identifying microbial agent(s) in a mammalian biological sample, such as a human biological sample, after extracting nucleic acid from the sample. In other embodiments, direct detection includes identifying microbial agent(s) in a human biological sample after human nucleic acid has been separated and removed from extracted nucleic acid.

Microbial Agent

A microbial agent as used herein is any microorganism. In some embodiments, the microbial agent is a bacterium. In other embodiments, the microbial agent is a fungus. In some embodiments, the microbial agent is a species selected from the group consisting of *Mycobacterium, Streptococcus, Staphylococcus, Burkholderia, Enterococcus*, and *Pseudomonas*.

A target sequence as described herein may represent one or more individual exon(s) or portion(s) of exon(s) of a microbial gene or one or more portions of a microbial mRNA. A target sequence also may include the promoter region and/or one or more introns of a microbial agent gene.

In some embodiments the target sequence represents the entire gene or the entire coding region. In some embodiments, the target sequence represents the entire coding region and at least one intron or a portion thereof and an adjacent region located immediately upstream (in the 5' direction) of the coding sequence. The adjacent, upstream region may consist of from about 100 nucleotides up to about 500, 750, 1000, 1100, or 1200 nucleotides of the sequence located immediately upstream of the coding sequence. In some embodiments, the adjacent, upstream region comprises all or a portion of the promoter sequence.

Sample

A sample as used herein contains nucleic acid of microbial agent(s) in, or isolated from, any source. In some embodiments, the sample is a biological sample from a mammal. In specific embodiments, the mammal is a human.

In some embodiments, the biological sample is a body fluid or a tissue sample. In some embodiments the biological sample consists or comprises blood, plasma, sera, urine, feces, epidermal sample, vaginal sample, skin sample, cheek swab, sperm, amniotic fluid, cultured cells, bone marrow sample and/or chorionic villi, cultured cells, and combinations thereof.

In some embodiments, the biological sample is a fixed or frozen tissue. In some embodiments, the biological sample is whole blood of about 0.5 to 5 ml collected with EDTA, ACD or heparin as anti-coagulant. In some embodiments, the biological sample is amniotic fluid of 10-15 ml, cultured cells which are 80-100% confluent in two T-25 flasks, or 25 mg of chorionic villi.

In some embodiments, the sample contains one or more microbial agents. In some embodiments, the sample contains multiple microbial agents. In some embodiments, the sample contains a mixture of bacteria. In other embodiments, the sample contains a mixture of fungi. In other embodiments, the sample contains a mixture of bacterium/bacteria and fungus/fungi.

Processing methods to release or otherwise make available a nucleic acid for detection are well known in the art and may include steps of nucleic acid manipulation, e.g., preparing a cDNA by reverse transcription of RNA from a biological sample. In some embodiments, a sample taken from a patient is extracted using the MagNA Pure LC instrument or an equivalent tabletop instrument that performs rapid, cross-contamination-free preparation of nucleic acids and PCR setup. The instrument may utilize magnetic-bead technology and may be equipped with a robotic system and automatically isolates any type of nucleic acid. It further may be capable of processing up to 32 different samples in one batch. The enables consistent isolation of high-quality DNA or RNA.

Adapter Sequence

An adapter sequence (also referred to as a sequencing adapter) is ligated to the 5' end of the target specific sequence portion of the primer. This sequencing adapter is a short oligonucleotide of known sequence that can provide a priming site for both amplification and sequencing of the adjoining, unknown nucleic acid. As such, adapters allow binding of a fragment to a flow cell for high throughput, massively parallel sequencing, as described herein. Any adapter sequence may be included in a primer used in the present invention.

In some embodiments, all forward amplicons (i.e., amplicons extended from forward primers that hybridized with antisense strands of a target segment) contain the same adapter sequence. In some embodiments when double stranded sequencing is performed, all forward amplicons contain the same adapter sequence and all reverse amplicons (i.e., amplicons extended from reverse primers that hybridized with sense strands of a target segment) contain an adapter sequence that is different from the adapter sequence of the forward amplicons.

In some embodiments, the "forward" adapter sequence consists of or comprises: CCATCT-CATCCCTGCGTGTCTCCGACTCAG (SEQ ID NO:1) or a sequence 90%, 95%, 97%, 98%, or 99% identical to SEQ ID NO:1. and the reverse adapter sequence consists of or comprises CCTCTCTATGGGCAGTCGGTGAT (SEQ ID NO:2) or a sequence 90%, 95%, 97%, 98%, or 99% identical to SEQ ID NO:2. These sequences are provided in Table 1.

Other adapter sequences are known in the art. Some manufacturers recommend specific adapter sequences for use with the particular sequencing technology and machinery that they offer.

In some embodiments, when adapter-ligated and/or indexed primers are employed to amplify a target segment, the adapter sequence and/or index sequence gets incorporated into the amplicon (along with the target-specific primer sequence) during amplification. Therefore, the resulting amplicons are sequencing-competent and do not require the traditional library preparation protocol. Moreover, the presence of the index tag permits the differentiation of sequences from multiple sample sources.

In some embodiments, sequencing templates (amplicons) are prepared by emulsion-based clonal amplification of target segments using specialized fusion primers (containing an adapter sequence) and capture beads. A single adapter-bound fragment is attached to the surface of a bead, and an oil emulsion containing necessary amplification reagents is formed around the bead/fragment component. Parallel amplification of millions of beads with millions of single strand fragments produces a sequencer-ready library.

In some embodiments, the amplicons constituting the adapter-tagged (and, optionally, indexed) amplicon library are produced by polymerase chain reaction (PCR). In some embodiments, the amplicon library is generated using a multiplexed PCR approach, such as that disclosed in U.S. Pat. No. 8,092,996, incorporated by reference herein in its entirety.

In other embodiments, each nucleic acid target segment may be amplified with non-adapter-ligated and/or non-indexed primers and a sequencing adapter and/or an index sequence may be subsequently ligated to each of the resulting amplicons.

In some embodiments, sequencing by ligation method using a DNA ligase is applied to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method can utilize Life Technologies' SOLiD™ sequencers.

Multiplex Identifier

In some cases, amplicons from a single sample source further comprise an identical index sequence (also referred to as an index tag, a "barcode" or a multiplex identifier (MID)). In some cases, indexed amplicons are generated using primers (for example, forward primers and/or reverse primers) containing the index sequence. Such indexed primers may be included during library preparation as a "barcoding" tool to identify specific amplicons as originating from a particular sample source. Indexed amplicons from more than one sample source are quantified individually and then pooled prior to sequencing. As such, the use of index sequences permits multiple samples (i.e., samples from more than one sample source) to be pooled per sequencing run and the sample source subsequently ascertained based on the index sequence. Table 1 provides examples of MID sequences used in the methods described herein.

In some embodiments, amplicons from more than one sample source are pooled prior to high throughput sequencing. "Multiplexing" is the pooling of multiple adapter-tagged and indexed libraries into a single sequencing run. When indexed primer sets are used, this capability can be exploited for comparative studies. In some embodiments, amplicon libraries from up to 48 separate sources are pooled prior to sequencing.

High Throughput, Massively Parallel Sequencing

High throughput, massively parallel sequencing refers to sequencing methods that can generate multiple sequencing reactions of clonally amplified molecules and of single nucleic acid molecules in parallel. This allows increased throughput and yield of data. These methods are also known in the art as next generation sequencing (NGS) methods. NGS methods include, for example, sequencing-by-synthesis using reversible dye terminators, and sequencing-by-ligation.

In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing.

Non-limiting examples of commonly used NGS platforms include Apollo 324™ NGS Library Prep System (IntegenX, Pleasanton, United States), Ion Torrent™ (Life Technologies, Carlsbad, Calif.), miRNA BeadArray (Illumina, Inc.), Roche 454™ GS FLX™-Titanium (Roche Molecular Diagnostics, Germany), and ABI SOLiD™ System (Applied Biosystems, Foster City, Calif.). Following the production of an adapter tagged and, optionally indexed, amplicon library, the amplicons are sequenced using high throughput, massively parallel sequencing.

Kit and Primer(s)

The direct detection methods as described herein can be performed using a kit comprising any one or more of the following components: universal primer(s) (e.g., 16S rDNA and ITS rDNA); primer(s), including primer(s) comprising one or more of a target specific sequence, adapter sequence, MID, and tag; dNTP; and other components for amplifying nucleic acid, such as by PCR (including via high throughput, massively parallel sequencing). In some embodiments, the kit comprises components to extract human nucleic acid from a sample.

In some embodiments, the kit comprises any one or more of SEQ ID NOs: 1-335, as listed in Tables 1-10. The kit can include a primer or primer pair comprising any combination of the sequences listed in Tables 1-10, with or without additional nucleic acid(s). For example, SEQ ID NO:23 is a primer consisting of SEQ ID NO: 1 (Adapter A sequence) and SEQ ID NO:5 (MID1). However, a primer or primer pair as described herein can include SEQ ID NO:1 and SEQ ID NO:5 with additional nucleic acid(s) between the two sequences or flanking one or both sequences. In some embodiments, a primer or primer pair as described herein comprises a spacer between two or more of SEQ ID NOs: 1-335. Spacers are known in the art.

TABLE 1

Adapter, Tag, and Multiplex Identifier Sequences

| SEQ ID NO: | Name | Sequence |
|---|---|---|
| Adapter Sequences | | |
| 1 | Adapter A | CCATCTCATCCCTGCGTGTCTCCGACTCAG |
| 2 | Adapter P | CCTCTCTATGGGCAGTCGGTGAT |
| Tag Sequences | | |
| 3 | Forward Tag | ACACTGACGACATGGTTCTACA |
| 4 | Reverse Tag | TACGGTAGCAGAGACTTGGTCT |
| Multiplex Index Sequences | | |
| 5 | MID1 | ACGAGTGCGT |
| 6 | MID2 | ACGCTCGACA |
| 7 | MID3 | AGACGCACTC |
| 8 | MID4 | AGCACTGTAG |
| 9 | MID5 | ATCAGACACG |
| 10 | MID6 | ATATCGCGAG |
| 11 | MID7 | CGTGTCTCTA |

TABLE 1-continued

Adapter, Tag, and Multiplex Identifier Sequences

| SEQ ID NO: | Name | Sequence |
|---|---|---|
| 12 | MID8 | CTCGCGTGTC |
| 13 | MID9 | TAGTATCAGC |
| 14 | MID10 | TCTCTATGCG |
| 15 | MID11 | TGATACGTCT |
| 16 | MID12 | TACTGAGCTA |
| 17 | MID13 | CATAGTAGTG |
| 18 | MID14 | CGAGAGATAC |
| 19 | MID15 | ATACGACGTA |
| 20 | MID16 | TCACGTACTA |
| 21 | MID17 | CGTCTAGTAC |
| 22 | MID18 | TCTACGTAGC |

Primers with Adapter and Multiplex Index Sequences

| SEQ ID NO: | Name | Sequence |
|---|---|---|
| 23 | PGMA MID1 | CCATCTCATCCCTGCGTGTCTCCGACTCAGACGAGTGCGT |
| 24 | PGMA MID2 | CCATCTCATCCCTGCGTGTCTCCGACTCAGACGCTCGACA |
| 25 | PGMA MID3 | CCATCTCATCCCTGCGTGTCTCCGACTCAGAGACGCACTC |
| 26 | PGMA MID4 | CCATCTCATCCCTGCGTGTCTCCGACTCAGAGCACTGTAG |
| 27 | PGMA MID5 | CCATCTCATCCCTGCGTGTCTCCGACTCAGATCAGACACG |
| 28 | PGMA MID6 | CCATCTCATCCCTGCGTGTCTCCGACTCAGATATCGCGAG |
| 29 | PGMA MID7 | CCATCTCATCCCTGCGTGTCTCCGACTCAGCGTGTCTCTA |
| 30 | PGMA MID8 | CCATCTCATCCCTGCGTGTCTCCGACTCAGCTCGCGTGTC |
| 31 | PGMA MID9 | CCATCTCATCCCTGCGTGTCTCCGACTCAGTAGTATCAGC |
| 32 | PGMA MID10 | CCATCTCATCCCTGCGTGTCTCCGACTCAGTCTCTATGCG |
| 33 | PGMA MID11 | CCATCTCATCCCTGCGTGTCTCCGACTCAGTGATACGTCT |
| 34 | PGMA MID12 | CCATCTCATCCCTGCGTGTCTCCGACTCAGTACTGAGCTA |
| 35 | PGMA MID13 | CCATCTCATCCCTGCGTGTCTCCGACTCAGCATAGTAGTG |
| 36 | PGMA MID14 | CCATCTCATCCCTGCGTGTCTCCGACTCAGCGAGAGATAC |
| 37 | PGMA MID15 | CCATCTCATCCCTGCGTGTCTCCGACTCAGATACGACGTA |
| 38 | PGMA MID16 | CCATCTCATCCCTGCGTGTCTCCGACTCAGTCACGTACTA |
| 39 | PGMA MID1 Comp | ACGCACTCGTCTGAGTCGGAGACACGCAGGGATGAGATGG |
| 40 | PGMA MID2 Comp | TGTCGAGCGTCTGAGTCGGAGACACGCAGGGATGAGATGG |
| 41 | PGMA MID3 Comp | GAGTGCGTCTCTGAGTCGGAGACACGCAGGGATGAGATGG |
| 42 | PGMA MID4 Comp | CTACAGTGCTCTGAGTCGGAGACACGCAGGGATGAGATGG |
| 43 | PGMA MID5 Comp | CGTGTCTGATCTGAGTCGGAGACACGCAGGGATGAGATGG |
| 44 | PGMA MID6 Comp | CTCGCGATATCTGAGTCGGAGACACGCAGGGATGAGATGG |
| 45 | PGMA MID7 Comp | TAGAGACACGCTGAGTCGGAGACACGCAGGGATGAGATGG |
| 46 | PGMA MID8 Comp | GACACGCGAGCTGAGTCGGAGACACGCAGGGATGAGATGG |
| 47 | PGMA MID9 Comp | GCTGATACTACTGAGTCGGAGACACGCAGGGATGAGATGG |
| 48 | PGMA MID10 Comp | CGCATAGAGACTGAGTCGGAGACACGCAGGGATGAGATGG |
| 49 | PGMA MID11 Comp | AGACGTATCACTGAGTCGGAGACACGCAGGGATGAGATGG |
| 50 | PGMA MID12 Comp | TAGCTCAGTACTGAGTCGGAGACACGCAGGGATGAGATGG |
| 51 | PGMA MID13 Comp | CACTACTATGCTGAGTCGGAGACACGCAGGGATGAGATGG |
| 52 | PGMA MID14 Comp | GTATCTCTCGCTGAGTCGGAGACACGCAGGGATGAGATGG |
| 53 | PGMA MID15 Comp | TACGTCGTATCTGAGTCGGAGACACGCAGGGATGAGATGG |
| 54 | PGMA MID16 Comp | TAGTACGTGACTGAGTCGGAGACACGCAGGGATGAGATGG |

PCR2 Forward Primers
(Primers with Adapter A, MID, and Forward Tag)

| SEQ ID NO: | Name | Sequence |
|---|---|---|
| 55 | PGMA MID1 FT | CCATCTCATCCCTGCGTGTCTCCGACTCAGACGAGTGCGTACACTGACGACATGGTTCTACA |
| 56 | PGMA MID2 FT | CCATCTCATCCCTGCGTGTCTCCGACTCAGACGCTCGACAACACTGACGACATGGTTCTACA |
| 57 | PGMA MID3 FT | CCATCTCATCCCTGCGTGTCTCCGACTCAGAGACGCACTCACACTGACGACATGGTTCTACA |
| 58 | PGMA MID4 FT | CCATCTCATCCCTGCGTGTCTCCGACTCAGAGCACTGTAGACACTGACGACATGGTTCTACA |

TABLE 1-continued

Adapter, Tag, and Multiplex Identifier Sequences

| SEQ ID NO: | Name | Sequence |
|---|---|---|
| 59 | PGMA MID5 FT | CCATCTCATCCCTGCGTGTCTCCGACTCAGATCAGACACGACACTGACGACATGGTTCTACA |
| 60 | PGMA MID6 FT | CCATCTCATCCCTGCGTGTCTCCGACTCAGATATCGCGAGACACTGACGACATGGTTCTACA |
| 61 | PGMA MID7 FT | CCATCTCATCCCTGCGTGTCTCCGACTCAGCGTGTCTCTAACACTGACGACATGGTTCTACA |
| 62 | PGMA MID8 FT | CCATCTCATCCCTGCGTGTCTCCGACTCAGCTCGCGTGTCACACTGACGACATGGTTCTACA |
| 63 | PGMA MID9 FT | CCATCTCATCCCTGCGTGTCTCCGACTCAGTAGTATCAGCACACTGACGACATGGTTCTACA |
| 64 | PGMA MID10 FT | CCATCTCATCCCTGCGTGTCTCCGACTCAGTCTCTATGCGACACTGACGACATGGTTCTACA |
| 65 | PGMA MID11 FT | CCATCTCATCCCTGCGTGTCTCCGACTCAGTGATACGTCTACACTGACGACATGGTTCTACA |
| 66 | PGMA MID12 FT | CCATCTCATCCCTGCGTGTCTCCGACTCAGTACTGAGCTAACACTGACGACATGGTTCTACA |
| 67 | PGMA MID13 FT | CCATCTCATCCCTGCGTGTCTCCGACTCAGCATAGTAGTGACACTGACGACATGGTTCTACA |
| 68 | PGMA MID14 FT | CCATCTCATCCCTGCGTGTCTCCGACTCAGCGAGAGATACACACTGACGACATGGTTCTACA |
| 69 | PGMA MID15 FT | CCATCTCATCCCTGCGTGTCTCCGACTCAGATACGACGTAACACTGACGACATGGTTCTACA |
| 70 | PGMA MID16 FT | CCATCTCATCCCTGCGTGTCTCCGACTCAGTCACGTACTAACACTGACGACATGGTTCTACA |

Primer with Adapter P and Reverse Tag

| 71 | Primer P RT | CCTCTCTATGGGCAGTCGGTGATTACGGTAGCAGAGACTTGGTCT |

PCR2 Reverse Primers
(Primers with Adapter A, MID, and Reverse Tag)

| 72 | PGMA MID1 RT | CCATCTCATCCCTGCGTGTCTCCGACTCAGACGAGTGCGTTACGGTAGCAGAGACTTGGTCT |
| 73 | PGMA MID2 RT | CCATCTCATCCCTGCGTGTCTCCGACTCAGACGCTCGACATACGGTAGCAGAGACTTGGTCT |
| 74 | PGMA MID3 RT | CCATCTCATCCCTGCGTGTCTCCGACTCAGAGACGCACTCTACGGTAGCAGAGACTTGGTCT |
| 75 | PGMA MID4 RT | CCATCTCATCCCTGCGTGTCTCCGACTCAGAGCACTGTAGTACGGTAGCAGAGACTTGGTCT |
| 76 | PGMA MID5 RT | CCATCTCATCCCTGCGTGTCTCCGACTCAGATCAGACACGTACGGTAGCAGAGACTTGGTCT |
| 77 | PGMA MID6 RT | CCATCTCATCCCTGCGTGTCTCCGACTCAGATATCGCGAGTACGGTAGCAGAGACTTGGTCT |
| 78 | PGMA MID7 RT | CCATCTCATCCCTGCGTGTCTCCGACTCAGCGTGTCTCTATACGGTAGCAGAGACTTGGTCT |
| 79 | PGMA MID8 RT | CCATCTCATCCCTGCGTGTCTCCGACTCAGCTCGCGTGTCTACGGTAGCAGAGACTTGGTCT |
| 80 | PGMA MID9 RT | CCATCTCATCCCTGCGTGTCTCCGACTCAGTAGTATCAGCTACGGTAGCAGAGACTTGGTCT |
| 81 | PGMA MID10 RT | CCATCTCATCCCTGCGTGTCTCCGACTCAGTCTCTATGCGTACGGTAGCAGAGACTTGGTCT |
| 82 | PGMA MID11 RT | CCATCTCATCCCTGCGTGTCTCCGACTCAGTGATACGTCTTACGGTAGCAGAGACTTGGTCT |
| 83 | PGMA MID12 RT | CCATCTCATCCCTGCGTGTCTCCGACTCAGTACTGAGCTATACGGTAGCAGAGACTTGGTCT |
| 84 | PGMA MID13 RT | CCATCTCATCCCTGCGTGTCTCCGACTCAGCATAGTAGTGTACGGTAGCAGAGACTTGGTCT |
| 85 | PGMA MID14 RT | CCATCTCATCCCTGCGTGTCTCCGACTCAGCGAGAGATACTACGGTAGCAGAGACTTGGTCT |
| 86 | PGMA MID15 RT | CCATCTCATCCCTGCGTGTCTCCGACTCAGATACGACGTATACGGTAGCAGAGACTTGGTCT |
| 87 | PGMA MID16 RT | CCATCTCATCCCTGCGTGTCTCCGACTCAGTCACGTACTATACGGTAGCAGAGACTTGGTCT |

Primer with Adapter P and Forward Tag

| 88 | Primer P FT | CCTCTCTATGGGCAGTCGGTGATACACTGACGACATGGTTCTACA |

TABLE 2

16S Sequences

| SEQ ID NO: | Name | Sequence | |
|---|---|---|---|
| | | 16S V2 Set 2 | |
| 89 | 16S V2 F101a | GGCGGACGGGTGAGTAA | |
| 90 | 16S V2 F101b | GGCGAACGGGTGAGTAA | |
| 91 | 16S V2 F101c | GGCGCACGGGTGAGTAA | |
| 92 | 16S V2 F101d | GGCGGATGGGTGAGTAA | *Lactobacillus* |
| 93 | 16S V2 F101e | GGCAAACGGGTGAGTAA | *Megasphaera* |
| 94 | 16S V2 F101f | GGCGAACGGGCGAGTAA | *Mobiluncus* |
| 95 | 16S V2 F101g | GGCGAACGGCTGAGTAA | *Atopobium* |
| 96 | 16S V2 R356a | CACTGCTGCCTCCCGTAG | |
| 97 | 16S V2 R356b | TACTGCTGCCTCCCGTAG | |
| | | 16S V3 Set 2 | |
| 98 | 16S V3 F323a | GACACGGTCCAGACTCCTAC | |
| 99 | 16S V3 F323b | GACACGGCCCAGACTCCTAC | |
| 100 | 16S V3 F323c | GACACGGTCCAAACTCCTAC | *Bacillus* |
| 101 | 16S V3 F323d | GACACGGCCCAAACTCCTAC | *Lactobacillus* |
| 102 | 16S V3 F323e | GATACGGCCCAGACTCCTAC | Myco, Mob, Gard |
| 103 | 16S V3 R531a | ATTACCGCGGCTGCTG | |
| | | PCR1 V2 (Tag, Sequence Specific) | |
| 104 | Tag V2 F101a | ACACTGACGACATGGTTCTACA GGCGGACGGGTGAGTAA | |
| 105 | Tag V2 F101b | ACACTGACGACATGGTTCTACA GGCGAACGGGTGAGTAA | |
| 106 | Tag V2 F101c | ACACTGACGACATGGTTCTACA GGCGCACGGGTGAGTAA | |
| 107 | Tag V2 F101d | ACACTGACGACATGGTTCTACA GGCGGATGGGTGAGTAA | |
| 108 | Tag V2 F101e | ACACTGACGACATGGTTCTACA GGCAAACGGGTGAGTAA | |
| 109 | Tag V2 F101f | ACACTGACGACATGGTTCTACA GGCGAACGGGCGAGTAA | |
| 110 | Tag V2 F101g | ACACTGACGACATGGTTCTACA GGCGAACGGCTGAGTAA | |
| 111 | Tag V2 R356a | TACGGTAGCAGAGACTTGGTCT CACTGCTGCCTCCCGTAG | |
| 112 | Tag V2 R356b | TACGGTAGCAGAGACTTGGTCT TACTGCTGCCTCCCGTAG | |
| | | PCR1 V3 (Tag, Sequence Specific) | |
| 113 | Tag V3 F323a | ACACTGACGACATGGTTCTACA GACACGGTCCAGACTCCTAC | |
| 114 | Tag V3 F323b | ACACTGACGACATGGTTCTACA GACACGGCCCAGACTCCTAC | |
| 115 | Tag V3 F323c | ACACTGACGACATGGTTCTACA GACACGGTCCAAACTCCTAC | |

TABLE 2-continued

16S Sequences

| SEQ ID NO: | Name | Sequence |
|---|---|---|
| 116 | Tag V3 F323d | ACACTGACGACATGGTTCTACAGACACGGCCCAAACTCCTAC |
| 117 | Tag V3 F323e | ACACTGACGACATGGTTCTACAGATACGGCCCAGACTCCTAC |
| 118 | Tag V3 R531a | TACGGTAGCAGAGACTTGGTCTATTACCGCGGCTGCTG |

TABLE 3

ITS Sequences

| SEQ ID NO: | Name | Sequence |
|---|---|---|
| *ITS Sequences F and R Primer Pairs* | | |
| 119 | ITS1Fb | AAACTCGGTCATTTAGAGGAAGTAA |
| 120 | ITSR513 | GATGCCGGAACCAAGAGAT |
| 121 | ITSF329 | AACCTCCCACCCGTGTTTAT |
| 122 | ITSR533 | ATTTCGCTGCGTTCTTCATC |
| 123 | ITS1Fb | AAACTCGGTCATTTAGAGGAAGTAA |
| 124 | ITS2b | GCTGCGTTCTTCATCGATG |
| 125 | ITSF569 | ATCGAGTCTTTGAACGCACA |
| 126 | ITSR820 | CCTACCTGATCCGAGGTCAA |
| 127 | ITSF570 | TCGAGTCTTTGAACGCACAT |
| 128 | ITSR828 | CGGGTATCCCTACCTGATCC |
| *ITS Reading Set (Adapter A, MID or Adapter P)* | | |
| 129 | ITSPGM1FbA MID1 | CCATCTCATCCCTGCGTGTCTCCGACTCAGACGAGTGCGTAAACTCGGTCATTTAGAGGAAGTAA |
| 130 | ITSPGMR513P | CCTCTCTATGGGCAGTCGGTGATGATGCCGGAACCAAGAGAT |
| 131 | ITSPGMF329A MID1 | CCATCTCATCCCTGCGTGTCTCCGACTCAGACGAGTGCGTAACCTCCCACCCGTGTTTAT |
| 132 | ITSPGMR533P | CCTCTCTATGGGCAGTCGGTGATATTTCGCTGCGTTCTTCATC |
| 133 | ITSPGM1FbA MID1 | CCATCTCATCCCTGCGTGTCTCCGACTCAGACGAGTGCGTAAACTCGGTCATTTAGAGGAAGTAA |
| 134 | ITSPGM2bP | CCTCTCTATGGGCAGTCGGTGATGCTGCGTTCTTCATCGATG |
| 135 | ITSPGMF569A MID1 | CCATCTCATCCCTGCGTGTCTCCGACTCAGACGAGTGCGTATCGAGTCTTTGAACGCACA |
| 136 | ITSPGMR820P | CCTCTCTATGGGCAGTCGGTGATCCTACCTGATCCGAGGTCAA |
| 137 | ITSPGMF570A MID1 | CCATCTCATCCCTGCGTGTCTCCGACTCAGACGAGTGCGTTCGAGTCTTTGAACGCACAT |
| 138 | ITSPGMR828P | CCTCTCTATGGGCAGTCGGTGATCGGGTATCCCTACCTGATCC |
| *PCR1 (Tag, Sequence Specific)* | | |
| 335 | Tag ITS1Fb | ACACTGACGACATGGTTCTACAAAACTCGGTCATTTAGAGGAAGTAA |
| 336 | Tag ITS2b | TACGGTAGCAGAGACTTGGTCTGCTGCGTTCTTCATCGATG |
| 337 | Tag ITSF569 | ACACTGACGACATGGTTCTACAATCGAGTCTTTGAACGCACA |
| 338 | Tag ITSR820 | TACGGTAGCAGAGACTTGGTCTCCTACCTGATCCGAGGTCAA |

TABLE 4

*Mycobacterium* Sequences

| SEQ ID NO: | Name | Sequence | Description |
|---|---|---|---|
| *Mycobacterium Fragment 1* | | | |
| 139 | MycoPGMF2649 | GCAAGGTCACCCCGAAG | |
| 140 | MycoPGMR2924 | CGATGACGCCCTTGTTG | |
| 141 | MycoPGMF2648 | GGCAAGGTCACCCCGAAGG | |
| 142 | MycoPGMR2934 | AGGATCTTGCCGATGACG | |

TABLE 4-continued

*Mycobacterium* Sequences

| SEQ ID NO: | Name | Sequence | Description |
|---|---|---|---|
| | | *Mycobacterium* Fragment 2 | |
| 143 | MycoPGM2F2898 | GACGCCACGGCAACAAG | |
| 144 | MycoPGM2F2899 | ACGCCACGGCAACAAG | |
| 145 | MycoPGM2R3337 | CAAGTGGTGCAGCTTCAGGATG | *Corynebacterium* |
| 146 | MycoPGM2R3337d | CARGTGGTGCAGCTTCAKGATG | |
| 147 | MycoPGM2R3169 | GGCGCCGTCGAACAC | |
| 148 | MycoPGM2R3169d | GGCRCCGTCGAACAC | |
| 149 | MycoPGM2R3169a | GGCACCGTCGAACAC | |
| 150 | MycoPGM2R3169b | GGCGCCGTCGAACAC | |
| | | *Mycobacterium* Fragment 3 | |
| 151 | MycoPGM2F3148 | CACCCCGGTGTTCGAC | |
| 152 | MycoPGM2R3391 | CTGGGTGATCATCGAGTACG | |
| | Fragment 1 Forward Reading Set (Adapter A or Adapter P) | | |
| 153 | MycoPGMF2649A | CCATCTCATCCCTGCGTGTCTCCGACTCAG GCAAGGTCACCCCGAAG | |
| 154 | MycoPGMR2924P | CCTCTCTATGGGCAGTCGGTGAT CGATGACGCCCTTGTTG | |
| 155 | MycoPGMF2648A | CCATCTCATCCCTGCGTGTCTCCGACTCAG GGCAAGGTCACCCCGAAGG | |
| 156 | MycoPGMR2934P | CCTCTCTATGGGCAGTCGGTGAT AGGATCTTGCCGATGACG | |
| 157 | MycoPGMF2649A MID1 | CCATCTCATCCCTGCGTGTCTCCGACTCAG ACGAGTGCGTGCAAGGTCACCCCGAAG | |
| | Fragment 1 Reverse Reading Set (Adapter P or Adapter A) | | |
| 158 | MycoPGMF2649P | CCTCTCTATGGGCAGTCGGTGAT GCAAGGTCACCCCGAAG | |
| 159 | MycoPGMR2924A | CCATCTCATCCCTGCGTGTCTCCGACTCAG CGATGACGCCCTTGTTG | |
| 160 | MycoPGMF2648P | CCTCTCTATGGGCAGTCGGTGAT GGCAAGGTCACCCCGAAGG | |
| 161 | MycoPGMR2934A | CCATCTCATCCCTGCGTGTCTCCGACTCAG AGGATCTTGCCGATGACG | |
| | Fragment 2 Forward Reading Set (Adapter A or Adapter P) | | |
| 162 | MycoPGM2F2898A | CCATCTCATCCCTGCGTGTCTCCGACTCAG GACGCCACGGCAACAAG | |
| 163 | MycoPGM2F2899A | CCATCTCATCCCTGCGTGTCTCCGACTCAG ACGCCACGGCAACAAG | |
| 164 | MycoPGM2R3337P | CCTCTCTATGGGCAGTCGGTGAT CAAGTGGTGCAGCTTCAGGATG | |
| 165 | MycoPGM2R3337dP | CCTCTCTATGGGCAGTCGGTGAT CARGTGGTGCAGCTTCAKGATG | |
| 166 | MycoPGM2R3169P | CCTCTCTATGGGCAGTCGGTGAT GGCGCCGTCGAACAC | |
| 167 | MycoPGM2R3169dP | CCTCTCTATGGGCAGTCGGTGAT GGCRCCGTCGAACAC | |

TABLE 4-continued

Mycobacterium Sequences

| SEQ ID NO: | Name | Sequence | Description |
|---|---|---|---|
| 168 | MycoPGM2F2898A MID1 | CCATCTCATCCCTGCGTGTCTCCGACTCAG ACGAGTGCGTGACGCCACGGCAACAAG | |
| 169 | MycoPGM2F2899A MID1 | CCATCTCATCCCTGCGTGTCTCCGACTCAG ACGAGTGCGTACGCCACGGCAACAAG | |

Fragment 2 Reverse Reading Set (Adapter P or Adapter A)

| SEQ ID NO: | Name | Sequence | Description |
|---|---|---|---|
| 170 | MycoPGM2F2898P | CCTCTCTATGGGCAGTCGGTGAT GACGCCACGGCAACAAG | |
| 171 | MycoPGM2F2899P | CCTCTCTATGGGCAGTCGGTGAT ACGCCACGGCAACAAG | |
| 172 | MycoPGM2R3337A | CCATCTCATCCCTGCGTGTCTCCGACTCAG CAAGTGGTGCAGCTTCAGGATG | |
| 173 | MycoPGM2R3337dA | CCATCTCATCCCTGCGTGTCTCCGACTCAG CARGTGGTGCAGCTTCAKGATG | |
| 174 | MycoPGM2R3169A | CCATCTCATCCCTGCGTGTCTCCGACTCAG GGCGCCGTCGAACAC | |
| 175 | MycoPGM2R3169dA | CCATCTCATCCCTGCGTGTCTCCGACTCAG GGCRCCGTCGAACAC | |

Fragment 3 Forward Reading Set (Adapter A or Adapter P)

| SEQ ID NO: | Name | Sequence | Description |
|---|---|---|---|
| 176 | MycoPGM2F3148A | CCATCTCATCCCTGCGTGTCTCCGACTCAG CACCCCGGTGTTCGAC | |
| 177 | MycoPGM2R3391P | CCTCTCTATGGGCAGTCGGTGAT CTGGGTGATCATCGAGTACG | |
| 178 | MycoPGM2F3148A MID1 | CCATCTCATCCCTGCGTGTCTCCGACTCAG ACGAGTGCGTCACCCCGGTGTTCGAC | |

Fragment 3 Reverse Reading Set (Adapter P or Adapter A)

| SEQ ID NO: | Name | Sequence | Description |
|---|---|---|---|
| 179 | MycoPGM2F3148P | CCTCTCTATGGGCAGTCGGTGAT CACCCCGGTGTTCGAC | |
| 180 | MycoPGM2R3391A | CCATCTCATCCCTGCGTGTCTCCGACTCAG CTGGGTGATCATCGAGTACG | |

TABLE 5

Streptococcus Sequences

| SEQ ID NO: | Name | Sequence | Description |
|---|---|---|---|
| | | Streptococcus Fragment 1 | |
| 181 | StrepF1475a | CCTTGGGACCTGGTGGTT | saliv therm mitisB oralis suis anginosus |
| 182 | StrepF1475b | CCTTAGGACCTGGTGGTT | pyog dysgalac canis equi agalac pneumo sang |
| 183 | StrepF1475c | GCTTTAGGTCCTGGTGGTT | mutans |
| 184 | StrepF1475d | CCTTGGGGCCTGGTGGTT | mitisB |
| 185 | StrepF1475e | CCTTAGGGCCTGGTGGTT | Parasanguinis |
| 186 | StrepR1720a | CTTCTTCGTCGGCAGTCAAC | saliv therm pyog canis |

TABLE 5-continued

Streptococcus Sequences

| SEQ ID NO: | Name | Sequence | Description |
|---|---|---|---|
| 187 | StrepR1720b | CTTCTTCATCAGCAGTCAACC | pyog2 agalac dysgalac |
| 188 | StrepR1720c | CTTCTTCATCAGCAGTTAGC | equi |
| 189 | StrepR1720d | CTTCTTCATCAGCAGTAAGC | mutans |
| 190 | StrepR1720e | CTTCTTCATCAGCTGTCAAC | pneumo |
| 191 | StrepR1720f | CTTCTTCATCGGCTGTCAAC | mitis oralis paras suis |
| 192 | StrepR1720g | CTTCCTCGTCAGCGGTCAAC | sang |
| 193 | StrepR1720h | CTTCTTCGTCCGCTGTCAGC | anginosus |
| 194 | StrepR1720i | CTTCTTCATCCGCTGTTAGC | intermedius |

Streptococcus Fragment 2

| SEQ ID NO: | Name | Sequence | Description |
|---|---|---|---|
| 195 | StrepF1875a | TGCGACAGCATGTATTCCTT | |
| 196 | StrepF1875b | CGCAACAGCATGTATTCCTT | agalac |
| 197 | StrepF1875c | TGCAACGGCATGTATTCCTT | pyogenes dysgalac canis |
| 198 | StrepF1875d | GGCAACGGCATGTATTCCTT | intermedius |
| 199 | StrepR2148a | TGAGTTTGAACGACGGAATTT | saliv therm pyog dysgalac pneumo mitisB paras |
| 200 | StrepR2148b | TGAGTTGGAGCGACGGAATTT | canis |
| 201 | StrepR2148c | AGAGTTTGAACGGCGGAATTT | equi anginosus |
| 202 | StrepR2148d | AGAGTTAGAACGACGGAATTT | mutans |
| 203 | StrepR2148e | TGAGTTTGAACGGCGGAATTT | agalactie |
| 204 | StrepR2148f | TGAGTTAGAACGACGGAATTT | mitis oralis |
| 205 | StrepR2148g | TGAGTTAGAACGGCGGAATTT | sang intermedius |

Streptococcus Fragment 3

| SEQ ID NO: | Name | Sequence | Description |
|---|---|---|---|
| 206 | StrepF2885a | TGAACATCGGTCAGGTTATGG | salivarus suis |
| 207 | StrepF2885b | TGAACATTGGTCAGGTTATGG | thermo dysgalac sanguin |
| 208 | StrepF2885c | TGAATATTGGTCAGGTTATGG | pyogenes |
| 209 | StrepF2885d | TGAATATCGGTCAGGTTATGG | pneumo mitis oralis paras |
| 210 | StrepF2885e | TGAACATCGGACAAGTTATGG | canis |
| 211 | StrepF2885f | TGAACATTGGACAGGTTATGG | equi |
| 212 | StrepF2885g | TGAACATTGGGCAAGTTATGG | mutans |
| 213 | StrepF2885h | TGAATATCGGACAAGTTATGG | agalac intermedius |
| 214 | StrepF2885i | TGAATATTGGTCAAGTTATGG | anginosus |
| 215 | StrepR3134a | TGAAGTTTATCATCAACCATGTG | salivarus thermo pyog dysgal canis suis |
| 216 | StrepR3134b | TGCAATTTATCATCAACCATGTG | mutans mitis oralis |
| 217 | StrepR3134c | TGCAACTTATCATCAACCATGTG | agalac |

TABLE 5-continued

Streptococcus Sequences

| SEQ ID NO: | Name | Sequence | Description |
|---|---|---|---|
| 218 | StrepR3134d | TGAAGCTTATCATCTACCATGTG | intermedius |
| 219 | StrepR3134e | TGGAGTTTATCATCTACCATGTG | sang |
| 220 | StrepR3134f | TGAAGCTTATCATCAACCATGTG | equi |
| 221 | StrepR3134g | TGCAATTTATCGTCAACCATGTG | pneumo |
| 222 | StrepR3134h | TGGAGCTTATCATCAACCATGTG | anginosus |

Streptococcus Fragment 4

| 223 | StrepF3106a | CTTCACCACATGGTTGATGATAA | saliv thermo pyog mutans paras suis equi |
| 224 | StrepF3106b | CTCCACCACATGGTTGATGATAA | dysgalac canis mitis oralis |
| 225 | StrepF3106c | CTCCACCACATGGTTGACGATAA | pneumo |
| 226 | StrepF3106d | CTCCACCACATGGTAGATGATAA | sang |
| 227 | StrepF3106e | CTTCACCACATGGTAGATGATAA | intermed |
| 228 | StrepR3366a | TTCTGGTACACCTGGTTTTGG | saliv thermo pyog dysgalac paras |
| 229 | StrepR3366b | TTCTGGCACACCTGGTTTTGG | canis sang |
| 230 | StrepR3366c | TTCTGGAACACCTGGTTTTGG | agalac pneumo mitis oralis suis anginosus |
| 231 | StrepR3366d | TTCTGGGACACCTGGTTTTGG | intermed |
| 232 | StrepR3366e | TTCTGGTACACCAGGCTTTGG | equi |
| 233 | StrepR3366f | TTCTGGTACCCCTGGTTTTGG | mutans |

PGM Fragment 2 Set (Adapter A, MID or Adapter P)

| 234 | StrepPGMF1875a MID1 | CCATCTCATCCCTGCGTGTCTCCGACTCAG ACGAGTGCGT | |
| 235 | StrepPGMF1875b MID1 | CCATCTCATCCCTGCGTGTCTCCGACTCAG ACGAGTGCGT | |
| 236 | StrepPGMF1875c MID1 | CCATCTCATCCCTGCGTGTCTCCGACTCAG ACGAGTGCGT | |
| 237 | StrepPGMF1875d MID1 | CCATCTCATCCCTGCGTGTCTCCGACTCAG ACGAGTGCGT | |
| 238 | StrepPGMR2148a | CCTCTCTATGGGCAGTCGGTGAT | |
| 239 | StrepPGMR2148b | CCTCTCTATGGGCAGTCGGTGAT | |
| 240 | StrepPGMR2148c | CCTCTCTATGGGCAGTCGGTGAT | |
| 241 | StrepPGMR2148d | CCTCTCTATGGGCAGTCGGTGAT | |
| 242 | StrepPGMR2148e | CCTCTCTATGGGCAGTCGGTGAT | |
| 243 | StrepPGMR2148f | CCTCTCTATGGGCAGTCGGTGAT | |
| 244 | StrepPGMR2148g | CCTCTCTATGGGCAGTCGGTGAT | |

PGM Fragment 3 Set (Adapter A, MID or Adapter P)

| 245 | StrepPGMF2885a MID1 | CCATCTCATCCCTGCGTGTCTCCGACTCAG ACGAGTGCGT | |
| 246 | StrepPGMF2885b MID1 | CCATCTCATCCCTGCGTGTCTCCGACTCAG ACGAGTGCGT | |

TABLE 5-continued

Streptococcus Sequences

| SEQ ID NO: | Name | Sequence | Description |
|---|---|---|---|
| 247 | StrepPGMF2885c MID1 | CCATCTCATCCCTGCGTGTCTCCGACTCAG ACGAGTGCGT | |
| 248 | StrepPGMF2885d MID1 | CCATCTCATCCCTGCGTGTCTCCGACTCAG ACGAGTGCGT | |
| 249 | StrepPGMF2885e MID1 | CCATCTCATCCCTGCGTGTCTCCGACTCAG ACGAGTGCGT | |
| 250 | StrepPGMF2885f MID1 | CCATCTCATCCCTGCGTGTCTCCGACTCAG ACGAGTGCGT | |
| 251 | StrepPGMF2885g MID1 | CCATCTCATCCCTGCGTGTCTCCGACTCAG ACGAGTGCGT | |
| 252 | StrepPGMF2885h MID1 | CCATCTCATCCCTGCGTGTCTCCGACTCAG ACGAGTGCGT | |
| 253 | StrepPGMF2885i MID1 | CCATCTCATCCCTGCGTGTCTCCGACTCAG ACGAGTGCGT | |
| 254 | StrepPGMR3134a | CCTCTCTATGGGCAGTCGGTGAT | |
| 255 | StrepPGMR3134b | CCTCTCTATGGGCAGTCGGTGAT | |
| 256 | StrepPGMR3134c | CCTCTCTATGGGCAGTCGGTGAT | |
| 257 | StrepPGMR3134d | CCTCTCTATGGGCAGTCGGTGAT | |
| 258 | StrepPGMR3134e | CCTCTCTATGGGCAGTCGGTGAT | |
| 259 | StrepPGMR3134f | CCTCTCTATGGGCAGTCGGTGAT | |
| 260 | StrepPGMR3134g | CCTCTCTATGGGCAGTCGGTGAT | |
| 261 | StrepPGMR3134h | CCTCTCTATGGGCAGTCGGTGAT | |
| PGM Fragment 4 Set (Adapter A, MID or Adapter P) | | | |
| 262 | StrepPGMF3106a MID1 | CCATCTCATCCCTGCGTGTCTCCGACTCAG ACGAGTGCGT | |
| 263 | StrepPGMF3106b MID1 | CCATCTCATCCCTGCGTGTCTCCGACTCAG ACGAGTGCGT | |
| 264 | StrepPGMF3106c MID1 | CCATCTCATCCCTGCGTGTCTCCGACTCAG ACGAGTGCGT | |
| 265 | StrepPGMF3106d MID1 | CCATCTCATCCCTGCGTGTCTCCGACTCAG ACGAGTGCGT | |
| 266 | StrepPGMF3106e MID1 | CCATCTCATCCCTGCGTGTCTCCGACTCAG ACGAGTGCGT | |
| 267 | StrepPGMR3366a | CCTCTCTATGGGCAGTCGGTGAT | |
| 268 | StrepPGMR3366b | CCTCTCTATGGGCAGTCGGTGAT | |
| 269 | StrepPGMR3366c | CCTCTCTATGGGCAGTCGGTGAT | |
| 270 | StrepPGMR3366d | CCTCTCTATGGGCAGTCGGTGAT | |
| 271 | StrepPGMR3366e | CCTCTCTATGGGCAGTCGGTGAT | |
| 272 | StrepPGMR3366f | CCTCTCTATGGGCAGTCGGTGAT | |

TABLE 6

*Staphylococcus* Sequences

| SEQ ID NO: | Name | Sequence | Description |
|---|---|---|---|
| *Staphylococcus* Fragment 1 | | | |
| 273 | StaphF44a | GAAACTACGCGAGAATTTCAGAAG | aureus, lugdunensis |
| 274 | StaphF44b | GAAATTACGCGAGAATTTCAGAAG | epidermidis, capitis |
| 275 | StaphF44c | GAAATTATGCGAGAATTTCAGAAG | haemolyticus |
| 276 | StaphF44d | GAAACTATGCGAGAATTTCAGAGG | saprophyticus |
| 277 | StaphR278a | CGAAGAGGTGCAGCATAAGTAG | |
| 278 | StaphR278b | CGTAATGGTGCCGCGTATGTTG | intermedius |
| 279 | StaphR278c | CGTAGAGGTGCAGAATACGTTG | saprophyticus |
| 280 | StaphF18a | CCAATATGGAAGACATCGTAAACG | |
| *Staphylococcus* Fragment 2 | | | |
| 281 | StaphF1251a | CCAATTCCGTATCGGTTTATC | |
| 282 | StaphF1251b | CCAATTCCGTATTGGTTTATC | lugdunensis, saprophyticus |
| 283 | StaphR1505a | ACTTCCATTTGAGCACGTTC | |
| 284 | StaphR1505b | ACTTCCATTTGGGCACGTTC | caprae |
| 285 | StaphR1505c | ACTTCCATTTGTGCACGTTC | lugdunensis |
| *Staphylococcus* Fragment 3 | | | |
| 286 | StaphF1484a | GTGAACGTGCTCAAATGGAAG | |
| 287 | StaphF1484b | GTGAACGTGCCCAAATGGAAG | caprae |
| 288 | StaphF1484c | GTGAACGTGCACAAATGGAAG | lugdunensis |
| 289 | StaphR1715a | ACATAGCTATCTTCTTCATCAGC | |
| 290 | StaphR1715b | ACGTAACTATCCTCTTCATCAGC | epidermidis |
| 291 | StaphR1715c | ACATAGCTATCCTCTTCATCAGC | epidermidis |
| 292 | StaphR1715d | ACATAGCTATCTTCTTCGTCAGC | aureus |
| 293 | StaphR1715e | ACATAACTGTCTTCTTCATCAGC | lugdunensis |
| *Staphylococcus* Fragment 4 | | | |
| 294 | StaphF3224a | TCGGTGAGATGGAGGTATGG | |
| 295 | StaphF3224b | TCGGTGAGATGGAAGTATGG | lugdunensis |
| 296 | StaphF3224c | TCGGTGAAATGGAAGTATGG | saprophyticus |
| 297 | StaphR3388a | CTCGGAATGATTCTGGAACAC | |
| 298 | StaphR3388b | CTCGGAATGATTCAGGAACAC | intermedius, capitis, lugdunensis, saprophyticus |

TABLE 7

Burkholderia Sequences

| SEQ ID NO: | Name | Sequence |
|---|---|---|
| 299 | BUR3 | GAAGAAGCAGTTCGGCAA |
| 300 | BUR4 | GAGTCGATGACGATCAT |
| 301 | recAF1 | CCACGCTCACGCTGCAGG |
| 302 | recAR1 | CGAGCCCGAGCGCACCAG |
| 303 | recAF2 | CGAAGGCGAGATGGGCG |
| 304 | recAR2 | TCGAGACGCACCGACG |
| 305 | recAF3 | GTGCAGGCGAAGATCGTCG |
| 306 | recAR3 | CCATCGCCTCGGCTTCG |

TABLE 8

Enterococcus Sequences

| SEQ ID NO: | Name | Sequence |
|---|---|---|
| 307 | tufF1 | GGCGGACGTCACACTCCATTC |
| 308 | tufR1 | CCGTCTTCGATAGCGATTGGGTGG |
| 309 | tufF2 | GGTTGCTCGTGAAGACATCCAAC |
| 310 | tufR2 | CACCAGTAACGTCTGTTGTACGG |
| 311 | tufF3 | CAGGCGATGATGTTCCAGTTATCGC |
| 312 | tufR3 | GTAGCAACAGTACCACGTCCAGTG |

TABLE 9

Pseudomonas Sequences

| SEQ ID NO: | Name | Sequence |
|---|---|---|
| 313 | APrU 34 | TGTAAAACGACGGCCAGTGCNGGRTCYTTYTCYTGRCA |
| 314 | M13(21)34 | TGTAAAACGACGGCCAGT |
| 315 | UP1E 34 | CAGGAAACAGCTATGACCAYGSNGGNGGNARTTYRA |
| 316 | M13R 34 | CAGGAAACAGCTATGACC |
| 317 | gyrbF1 | CAGCTGGGACATCCTGGCC |
| 318 | gyrbR1 | TGAGGGATGTTGTTGGTAAAGCAC |
| 319 | gyrbF2 | GTGCTTTACCAACAACATCCCTCA |
| 320 | gyrbR2 | TGTCTTTGGTCTGGGAGCTGAAC |

TABLE 10

IDT Label Sequences

| SEQ ID NO: | Name | Sequence |
|---|---|---|
| 321 | Br2-F-MID2 | CCATCTCATCCCTGCGTGTCTCCGACTCAG ACGCTCGACAAGYGGCGIACGGGTGAGTAA |
| 322 | Br2-F-MID3 | CCATCTCATCCCTGCGTGTCTCCGACTCAG AGACGCACTCAGYGGCGIACGGGTGAGTAA |
| 323 | Br2-F-MID4 | CCATCTCATCCCTGCGTGTCTCCGACTCAG AGCACTGTAGAGYGGCGIACGGGTGAGTAA |
| 324 | Br2-F-MID5 | CCATCTCATCCCTGCGTGTCTCCGACTCAG ATCAGACACGAGYGGCGIACGGGTGAGTAA |
| 325 | Br2-F-MID6 | CCATCTCATCCCTGCGTGTCTCCGACTCAG ATATCGCGAGAGYGGCGIACGGGTGAGTAA |
| 326 | Br2-F-MID7 | CCATCTCATCCCTGCGTGTCTCCGACTCAG CGTGTCTCTAAGYGGCGIACGGGTGAGTAA |
| 327 | Br2-F-MID8 | CCATCTCATCCCTGCGTGTCTCCGACTCAG CTCGCGTGTCAGYGGCGIACGGGTGAGTAA |
| 328 | Br3-F-MID2 | CCATCTCATCCCTGCGTGTCTCCGACTCAG ACGCTCGACAACTCCTACGGGAGGCAGCAG |
| 329 | Br3-F-MID3 | CCATCTCATCCCTGCGTGTCTCCGACTCAG AGACGCACTCACTCCTACGGGAGGCAGCAG |
| 330 | Br3-F-MID4 | CCATCTCATCCCTGCGTGTCTCCGACTCAG AGCACTGTAGACTCCTACGGGAGGCAGCAG |
| 331 | Br3-F-MID5 | CCATCTCATCCCTGCGTGTCTCCGACTCAG ATCAGACACGACTCCTACGGGAGGCAGCAG |
| 332 | Br3-F-MID6 | CCATCTCATCCCTGCGTGTCTCCGACTCAG ATATCGCGAGACTCCTACGGGAGGCAGCAG |
| 333 | Br3-F-MID7 | CCATCTCATCCCTGCGTGTCTCCGACTCAG CGTGTCTCTAACTCCTACGGGAGGCAGCAG |
| 334 | Br3-F-MID8 | CCATCTCATCCCTGCGTGTCTCCGACTCAG ACGAGTGCGTACTCCTACGGGAGGCAGCAG |

The following examples serve to illustrate the present invention. The examples are in no way intended to limit the scope of the invention.

Example 1: Direct Detection Using Primers with Adapter Sequence and Target Specific Sequence A biological sample is obtained from a human individual and nucleic acid extracted using the MagNA Pure LC instrument (Roche Molecular Diagnostics, Germany). A post-extraction step is performed to remove human nucleic acid from the sample.

The remaining nucleic acid from the sample is amplified using universal 16S rDNA and ITS rDNA primers. The amplification is performed using PCR. The resulting amplified nucleic acid is then amplified again using PCR with bacterial or fungal specific DNA oligonucleotide primer pairs.

Next, primer pairs comprising both a target specific sequence (e.g., specific for a particular sequence within a microbial gene) and an adapter sequence are used to perform a third amplification process. The forward and reverse primers in the primer pairs contain different adapter sequences. The primers can optionally include a MID. This process attaches the adapter sequences to the microbial nucleic acid.

The amplicons are then sequenced using a high throughput, massively parallel platform to identify the nucleic acid sequence of the microbial agent(s) in the sample. The sequences are compared against a BLAST of the rDNA targets to identify the specific microbial agent(s) present in the sample.

Example 2: Direct Detection Using Primers with Adapter Sequence and Multiplex Identifier A biological sample is obtained from a human individual and nucleic acid extracted using the MagNA Pure LC instrument (Roche Molecular Diagnostics, Germany). A post-extraction step is performed to remove human nucleic acid from the sample.

The remaining nucleic acid from the sample is amplified using universal 16S rDNA and ITS rDNA primers. The amplification is performed using PCR. The resulting amplified nucleic acid is then amplified again using PCR with bacterial or fungal specific DNA oligonucleotide primer pairs comprising a target specific sequence and a tag.

Next, primer pairs comprising an adapter sequence and a MID are used to perform a third amplification process, in which the MID hybridizes to the tag from the second amplification process. The forward and reverse primers in the primer pairs contain different adapter sequences. This process attaches the adapter sequence to the microbial nucleic acid.

The amplicons are then sequenced using a high throughput, massively parallel platform to identify the nucleic acid sequence of the microbial agent(s) in the sample. The sequences are compared against a BLAST of the rDNA targets to identify the specific microbial agent(s) present in the sample.

Alternatively, bi-directional sequencing can be performed, in which the forward and reverse primers in each primer pair have the opposite adapter sequence attached thereto.

Example 3: Direct Detection Using Enzyme Ligation to Attach Adapter

A biological sample is obtained from a human individual and nucleic acid extracted using the MagNA Pure LC instrument (Roche Molecular Diagnostics, Germany). A post-extraction step is performed to remove human nucleic acid from the sample.

The remaining nucleic acid from the sample is amplified using universal 16S rDNA and ITS rDNA primers. The amplification is performed using PCR. The resulting amplified nucleic acid is then amplified again using PCR with bacterial or fungal specific DNA oligonucleotide primer pairs.

Next, enzyme ligation is performed to attached a nucleotide comprising an adapter sequence and MID to the microbial nucleic acid. The resulting adapter-tagged microbial nucleic acid is then amplified using a primer pair to produce amplicons.

The amplicons are then sequenced using a high throughput, massively parallel platform to identify the nucleic acid sequence of the microbial agent(s) in the sample. The sequences are compared against a BLAST of the rDNA targets to identify the specific microbial agent(s) present in the sample.

Example 4: Direct Identification of Different Microbial Species in Polymicrobial Samples A ~459 bp segment of the V3-V4 bacterial 16s rrna gene was amplified with target-specific PCR primers with 5' overhang adapters. The amplification mix contained the following ingredients in sufficient volume for a quarter plate and a half plate.

| Reagents | x1 (uL) | x30 (uL) | x60 (uL) |
|---|---|---|---|
| 16Sv3v4-F Primer (1 uM) | 5 | 150 | 300 |
| 16Sv3v4-R Primer (1 uM) | 5 | 150 | 300 |
| 2X KAPA HiFi HotStart Ready Mix | 12.5 | 375 | 750 |
| Total | 22.5 | 675 | 1,350 |

Index sequences and adapters were ligated to the 5' and 3' ends of the amplicons to allow for paired end sequencing. The library derived from 15 samples was normalized and pooled, and loaded onto a MiSeq® sequencer for clustering and paired-end sequencing with the 250 bp paired end sequencing chemistry and a nano-flow cell.

Paired-end reads were merged and quality-filtered. Sequences were dereplicated, singletons were discarded, and then sequences clustered into centroids with a radius of 2%. Operational taxonomic units (OTUs) constructed from the centroids for each sample were searched against the Living Tree Program database release 111, available at http://www.arb-silva.de/projects/living-tree/ and/or the NCBI 16S rrna sequence database. Species identifications and the relative abundance of each identified species in the samples tested were tabulated.

Results

Sequence Metrics 421,105 raw reads were obtained, 368,337 reads passed the quality filtering stage for a PF rate of 87.5%. 93% of reads had a median Q value >Q30. The read distribution was normally distributed between the 15 samples in the pooled library with 4.1%±1.9% (1 SD) reads per sample. The negative control did not have an appreciable number of detectable reads (Table 11).

The vast majority of merged paired end reads produced full length amplicon sequence of 465 bp, or 427 bp after the target-specific PCR primers were trimmed.

TABLE 11

Reads and Operational Taxonomics Units (OTUs) per Sample

| Sample | Description | % of PF reads | reads clustered in OTUs | OTUs (>0.5%) |
|---|---|---|---|---|
| M1 | mixed organisms | 4.37 | 13681 | 7 |
| M2 | mixed organisms | 4.05 | 11764 | 14 |
| M3 | mixed organisms | 6.71 | 19967 | 8 |
| M4 | mixed organisms | 3.65 | 10087 | 11 |
| M5 | mixed organisms | 7.77 | 19821 | 8 |
| M6 | mixed organisms | 3.30 | 7232 | 6 |
| S1 | pure sample | 5.55 | 19673 | 1 |
| S2 | pure sample | 2.51 | 8874 | 1 |
| S3 | pure sample | 4.39 | 15577 | 2 |
| S4 | pure sample | 2.27 | 8073 | 1 |
| S5 | pure sample | 6.78 | 23824 | 1 |
| S6 | pure sample | 3.05 | 10899 | 1 |
| P1 | patient sample | 2.78 | 9731 | 1 |
| P2 | patient sample | 1.46 | 5147 | 1 |
| P3 | patient sample | 2.21 | 7705 | 1 |
| NEG | Negative Ctrl | 0.007 | NA | NA |

Organism Identification is shown in Table 12 below:

TABLE 12

Identification of Pure (S1-S6) and Patient (P1-P3) Samples

| Sample | Identification | Align (bp) | Match | % of Reads | Reads (N) | Experimental Input |
|---|---|---|---|---|---|---|
| P1_S13 | Pseudomonas_aeruginosa | 425 | 100% | 100% | 9731 | Pseudomonas aeruginosa |
| P2_S14 | Neisseria_sicca | 425 | 99.5% | 100% | 5147 | Neisseria sicca |
| P3_S15 | Bacillus_cereus | 425 | 100% | 100% | 7705 | Bacillus cereus |
| S1_S7 | Neisseria_lactamica | 425 | 100% | 100% | 19673 | Neisseria lactamica |
| S2_S8 | Acinetobacter_baumannii | 425 | 100% | 100% | 8874 | Acinetobacter baumannii |
| S3_S9 | Salmonella_enterica | 425 | 100% | 69.0% | 10753 | Salmonella cholereasuis |
| S3_S9 | Enterobacter_cloacae | 425 | 99.5% | 31.0% | 4824 | |
| S4_S10 | E. fergusonii/E. coli/Shigella | 425 | 100% | 100% | 8073 | Shigella sonnei |
| S5_S11 | Bordetella_parapertussis | 425 | 100% | 100% | 23824 | Bordetella parapertussis |
| S6_S12 | E. fergusonii/E. coli/Shigella | 425 | 100% | 100% | 10899 | E. coli |

The bioinformatic pipeline successfully identified the input species in the 6 pure samples and 3 patient samples (Table 12). Sample 3 appeared to contain a mixture of two species at a 2:1 ratio. The origin of the second species (*E. cloacae*) is not known.

Table 13 below demonstrates successful recovery of most input species from the mixed samples. *E. cloacae*, used in samples M1 and M2, appeared as a contaminant in samples M3 and M5.

TABLE 13

Identification of Six Mixed Bacterial Samples

| Sample | OTUId | Reads | Pct | Identity | Input | |
|---|---|---|---|---|---|---|
| M1_S1 | OTU_1 | 5580 | 40.8% | Acinetobacter_baumannii | Acinetobacter baumannii | |
| M1_S1 | OTU_2 | 2480 | 18.1% | E. fergusonii/E. coli/Shigella | Escherichia coli | Shigella sonnei |
| M1_S1 | OTU_3 | 2047 | 15.0% | Enterobacter_aerogenes | Enterobacter aerogenes | |
| M1_S1 | OTU_5 | 1614 | 11.8% | Enterobacter_cloacae | Enterobacter cloacae | |
| M1_S1 | OTU_4 | 861 | 6.3% | Bordetella_pertussis | Bordetella pertussis | |
| M1_S1 | OTU_6 | 573 | 4.2% | Salmonella_enterica | Salmonella choleraesuis | |
| M1_S1 | OTU_7 | 518 | 3.8% | Klebsiella_variicola | Klebsiella pneumoniae Nocardia farcinica | |
| M2_S2 | OTU_1 | 3984 | 33.9% | Staphylococcus epidermidis/capitis | Staphylococcus epidermidis | Staphylococcus aureus |
| M2_S2 | OTU_15 | 1121 | 9.5% | Staphylococcus_saprophyticus | Staphylococcus saprophyticus | |
| M2_S2 | OTU_3 | 1058 | 9.0% | Streptococcus_pyogenes | Strep pyogenes group a | |
| M2_S2 | OTU_2 | 1032 | 8.8% | Acinetobacter_baumannii | Acinetobacter baumannii | |
| M2_S2 | OTU_5 | 934 | 7.9% | E. fergusonii/E. coli/Shigella | Shigella sonnei | Escherichia coli |
| M2_S2 | OTU_6 | 807 | 6.9% | Streptococcus_agalactiae | Strep agalactiae group b | |
| M2_S2 | OTU_4 | 742 | 6.3% | Neisseria_lactamica | Neisseria lactamica | |
| M2_S2 | OTU_7 | 574 | 4.9% | Proteus_mirabilis | Proteus mirabilis | |
| M2_S2 | OTU_8 | 416 | 3.5% | Enterobacter_aerogenes | Enterobacter aerogenes | |
| M2_S2 | OTU_9 | 296 | 2.5% | Enterobacter_cloacae | Enterobacter cloacae | |
| M2_S2 | OTU_11 | 274 | 2.3% | Haemophilus_aegyptius | Haemophilus influenzae | |
| M2_S2 | OTU_12 | 179 | 1.5% | Bordetella_pertussis | Bordetella parapertussis | Bordetella pertussis |
| M2_S2 | OTU_10 | 166 | 1.4% | Pseudomonas aeruginosa | Pseudomonas aeruginosa | |
| M2_S2 | OTU_13 | 108 | 0.9% | Salmonella_enterica | Salmonella choleraesuis | |
| M2_S2 | OTU_14 | 73 | 0.6% | Klebsiella_variicola | Klebsiella pneumoniae Ochrobactrum anthropi Camphylobacter jejuni | |
| M3_S3 | OTU_1 | 7103 | 35.6% | Staphylococcus_capitis | Staphylococcus aureus | |
| | OTU_6 | 4117 | 20.6% | Staphylococcus_saprophyticus | Staphylococcus saprophyticus | |
| | OTU_2 | 3380 | 16.9% | Proteus_mirabilis | Proteus mirabilis | |
| | OTU_3 | 2082 | 10.4% | Streptococcus_agalactiae | Strep agalactiae group b | |
| | OTU_4 | 1396 | 7.0% | E. fergusonii/E. coli/Shigella | Escherichia coli | |
| | OTU_5 | 1046 | 5.2% | Pseudomonas aeruginosa | Pseudomonas aeruginosa | |
| | OTU_7 | 574 | 2.9% | Salmonella_enterica | Salmonella choleraesuis | |
| | OTU_8 | 269 | 1.3% | Enterobacter_cloacae | | |
| M4_S4 | OTU_1 | 3999 | 39.6% | Staphylococcus epidermidis/capitis | Staphylococcus epidermidis | |
| M4_S4 | OTU_2 | 1677 | 16.6% | Streptococcus_pyogenes | Strep pyogenes group a | |
| M4_S4 | OTU_3 | 1215 | 12.0% | Acinetobacter_baumannii | Acinetobacter baumannii | |
| M4_S4 | OTU_4 | 1069 | 10.6% | Neisseria_lactamica | Neisseria lactamica | |
| M4_S4 | OTU_5 | 533 | 5.3% | Enterobacter_aerogenes | Enterobacter aerogenes | |
| M4_S4 | OTU_6 | 490 | 4.9% | Haemophilus_aegyptius | Haemophilus influenzae | |
| M4_S4 | OTU_7 | 369 | 3.7% | Enterobacter_cloacae | Enterobacter cloacae | |
| M4_S4 | OTU_8 | 240 | 2.4% | Bordetella_pertussis | Bordetella parapertussis | Bordetella pertussis |
| M4_S4 | OTU_10 | 222 | 2.2% | E. fergusonii/E. coli/Shigella | Shigella sonnei | |
| M4_S4 | OTU_9 | 137 | 1.4% | Salmonella_enterica | Salmonella choleraesuis | |
| M4_S4 | OTU_11 | 132 | 1.3% | Klebsiella_variicola | Klebsiella pneumoniae Nocardia farcinica Ochrobactrum anthropi Camphylobacter jejuni | |

TABLE 13-continued

Identification of Six Mixed Bacterial Samples

| Sample | OTUId | Reads | Pct | Identity | Input | |
|---|---|---|---|---|---|---|
| M5_S5 | OTU_1 | 6110 | 437.7% | *Streptococcus_pyogenes* | *Strep pyogenes* group a | |
| M5_S5 | OTU_2 | 4336 | 310.6% | *Acinetobacter_baumannii* | *Acinetobacter baumannii* | |
| M5_S5 | OTU_3 | 3311 | 237.2% | *Neisseria_lactamica* | *Neisseria lactamica* | |
| M5_S5 | OTU_4 | 3151 | 225.7% | *Proteus_mirabilis* | *Proteus mirabilis* | |
| M5_S5 | OTU_5 | 1526 | 109.3% | *Haemophilus_aegyptius* | *Haemophilus influenzae* | |
| M5_S5 | OTU_6 | 720 | 51.6% | *E. fergusonii/E. coli/Shigella* | *Shigella sonnei* | |
| M5_S5 | OTU_7 | 453 | 32.4% | *Salmonella_enterica* | *Salmonella choleraesuis* | |
| M5_S5 | OTU_8 | 207 | 14.8% | *Enterobacter_cloacae* | | |
| | | | | | *Nocardia farcinica* | |
| | | | | | *Corynebacterium* | |
| M6_S6 | OTU_3 | 1697 | 23.5% | *Enterobacter_aerogenes* | *Enterobacter aerogenes* | |
| M6_S6 | OTU_4 | 1546 | 21.4% | *Bordetella_pertussis* | *Bordetella pertussis* | *Bordetella parapertussis* |
| M6_S6 | OTU_5 | 1206 | 16.7% | *Enterobacter_cloacae* | *Enterobacter cloacae* | |
| M6_S6 | OTU_2 | 1204 | 16.6% | *E. fergusonii/E. coli/Shigella* | *Escherichia coli* | |
| M6_S6 | OTU_1 | 1131 | 15.6% | *Pseudomonas_aeruginosa* | *Pseudomonas aeruginosa* | |
| M6_S6 | OTU_6 | 448 | 6.2% | *Klebsiella_variicola* | *Klebsiella pneumoniae* | |
| | | | | | *Camphylobacter jejuni* | |

These results demonstrate that the methods of the present application, which generate high quality paired-end sequence reads for sequence fragments of short length (in this case a 427 bp was used), accurately identify bacterial species in polymicrobial samples through rDNA amplification and sequencing.

Example 5: Direct Identification of Different Microbial Species in Polymicrobial Samples from Subjects Affected by Infections Difficult to Diagnose Biological fluids, including urine, sputum, vaginal fluid, sperm, blood and synovial fluid are collected from subjects affected by infections that are difficult to diagnose. The subjects are affected by chronic wound infections, lung infections, urinary tract infections, vaginal infections or infections of otherwise sterile body sites or of prosthetic implants. The samples are directly analyzed for the presence of gram-positive and gram-negative bacterial species without the need for culturing the bacterial colonies.

Results

Organisms that constitute 10% or more of a mixed population of three or more bacterial species that are present in the fluid sample are detected by 16s rDNA as described in Example 4 above.

That which is claimed is:

1. A method for determining the presence of one or more microbial agents in a polymicrobial sample without culturing the microbial agents, comprising
    (a) contacting a sample containing nucleic acids with an amplification reaction mixture, wherein the amplification reaction mixture comprises primers that specifically amplify at least one target sequence of bacterial 16S rDNA, at least one target sequence of fungal ITS rDNA, and at least one target sequence from each of *Mycobacterium* rpoB, *Staphylococcus* rpoB, *Streptococcus* rpoB, *Burkholderia* recA, *Enterococcus* tuf, and *Pseudomonas* gvrB, to generate an amplification reaction mixture containing the nucleic acids, wherein the sample has not been cultured;
    (b) subjecting the amplification reaction mixture containing the nucleic acids of step (a) to polymerase chain reaction (PCR) conditions to generate microbial amplicons;
    (c) producing adapter-tagged amplicons by attaching each of the microbial amplicons of step (b), if present, to nucleic acid adapters,
    (d) amplifying the adapter-tagged amplicons, if present, from step (c) to generate adapter-tagged amplicons;
    (e) sequencing the adapter-tagged amplicons, if present, from step (d) wherein a microbial agent is determined to be present in the sample if a microbial amplicon is present and the sequence of the non-adapter portion of an adapter tagged microbial amplicon is identical to a nucleotide fragment of bacterial 16S rDNA or fungal ITS rDNA, wherein:
        (i) the primers that specifically amplify at least one target sequence of bacterial 16S rDNA comprise forward primer and reverse primer selected from SEQ ID NOs 89-118;
        (ii) the primers that specifically amplify at least one target sequence of fungal ITS rDNA comprise forward primer and reverse primer selected from SEQ ID NOs 119-128;
        (iii) the primers that specifically amplify at least one target sequence of *Mycobacterium* rpoB comprise forward primer and reverse primer selected from SEQ ID NOs 139-152;
        (iv) the primers that specifically amplify at least one target sequence of *Streptococcus* rpoB comprise forward primer and reverse primer selected from SEQ ID NOs 181-233;
        (v) the primers that specifically amplify at least one target sequence of *Staphylococcus* rpoB comprise forward primer and reverse primer selected from SEQ ID NOs 273-298;
        (vi) the primers that specifically amplify at least one target sequence of *Burkholderia* recA comprise forward primer and reverse primer selected from SEQ ID NOs 299-306;
        (vii) the primers that specifically amplify at least one target sequence of *Enterococcus* tuf comprise forward primer and reverse primer selected from SEQ ID NOs 307-312; and
        (viii) the primers that specifically amplify at least one target sequence of *Pseudomonas* gvrB comprise forward primer and reverse primer selected from SEQ ID NOs 313-320; and
    (f) identifying the polymicrobial sample as containing one or more microbial agents when at least one microbial amplicon is present and the sequence of the non-adapter portion of an adapter tagged microbial amplicon is identical to a nucleotide fragment of bacterial 16S rDNA or fungal ITS rDNA.

2. The method of claim 1, wherein the method further comprises identifying the species of bacteria and/or fungus in the sample as *Mycobacterium, Staphylococcus, Streptococcus, Burkholderia, Enterococcus* and/or *Pseudomonas* gvrB.

3. The method of claim 1, wherein BLAST alignment analysis is performed to identify the species of bacteria and/or fungi present in the sample.

4. The method of claim 1, wherein a post-extraction step is performed on the nucleic acids to remove human DNA prior to combining with the amplification reaction mixture.

5. The method of claim 1 wherein each target region is amplified in a multiplexed reaction.

6. The method of claim 1, wherein the sample is a biological sample.

7. The method of claim 6, wherein the biological sample is a urine, sputum, vaginal fluid, sperm, blood or synovial fluid sample.

8. The method of claim 1, wherein the primers further comprise a tag sequence selected from the group consisting of SEQ ID NO:3 and SEQ ID NO:4.

9. The method of claim 1, wherein the adapter sequence is selected from the group consisting of SEQ ID NO:1 and SEQ ID NO:2.

10. The method of claim 1, wherein the adapters are attached via a primer comprising the adaptor sequence.

11. The method of claim 10, wherein the primer comprising the adaptor sequence further comprises a multiplex identifier sequence.

12. The method of claim 10, wherein the primer comprising the adaptor sequence further comprises a tag sequence selected from the group consisting of SEQ ID NO:3 and SEQ ID NO:4.

13. The method of claim 1 wherein:

(i) the primers that specifically amplify at least one target sequence of bacterial 16S rDNA comprise a forward primer selected from among SEQ ID NOs: 89-95, 98-102, 104-110, or 113-117 and a reverse primer selected from among SEQ ID NOs: 96, 97, 103, 111, 112, or 118;

(ii) the primers that specifically amplify at least one target sequence of fungal ITS rDNA comprise a forward primer selected from among SEQ ID NOs: 119, 121, 123, 125, 127, 129, 131, 133, 135, 137, 335, or 337 and a reverse primer selected from among SEQ ID NOs: 120, 122, 124, 126, 128, 130, 132, 134, 136, 138, 336, or 338;

(iii) the primers that specifically amplify at least one target sequence of *Mycobacterium* rpoB comprise a forward primer selected from among SEQ ID NOs: 139, 141, 143, 144, 151, 153, 155, 157, 158, 160, 162, 163, 168, 169, 170, 171, 176, 178, or 179 and a reverse primer selected from among SEQ ID NOs: 140, 142, 145-150, 152, 154, 156, 159, 161, 164-167, 172-175, 177, or 180;

(iv) the primers that specifically amplify at least one target sequence of *Streptococcus* rpoB comprise a forward primer selected from among SEQ ID NOs: 181-185, 195-198, 206-214, 223-227, 234-237, 245-253, or 262-266, and a reverse primer selected from among SEQ ID NOs: 186-194, 199-205, 215-222, 228-233, 238-244, 254-261, or 267-272;

(v) the primers that specifically amplify at least one target sequence of *Staphylococcus* rpoB comprise a forward primer selected from among SEQ ID NOs: 273-276, 280-282, 286-288, 294-296 and a reverse primer selected from among SEQ ID NOs: 277-279, 283-285, 289-293, 297-298;

(vi) the primers that specifically amplify at least one target sequence of *Burkholderia* recA comprise a forward primer having SEQ ID NOs: 299, 301, 303, or 305, and a reverse primer having SEQ ID NOs: 300, 302, 304, or 306;

(vii) the primers that specifically amplify at least one target sequence of *Enterococcus* tuf comprise a forward primer having SEQ ID NOs: 307, 309, or 311, and a reverse primer having SEQ ID NOs: 308, 310, or 312; and (viii) the primers that specifically amplify at least one target sequence of *Pseudomonas* gvrB comprise a forward primer having SEQ ID NOs: 317 or 319, and a reverse primer having SEQ ID NOs: 318 or 320.

\* \* \* \* \*